(12) United States Patent
Park et al.

(10) Patent No.: US 8,877,264 B2
(45) Date of Patent: Nov. 4, 2014

(54) COMPOSITION OF SKIN EXTERNAL APPLICATION CONTAINING GINSENG BERRY EXTRACTS

(75) Inventors: Chan Woong Park, Yongin-si (KR); Myeong Hoon Yeom, Yongin-si (KR); Jin Young Lee, Yongin-si (KR); Hee Young Jeon, Yongin-si (KR); Sang Jun Lee, Seongnam-si (KR); Nam Hoon Cho, Seongnam-si (KR); Dong Sung Lee, Anyang-si (KR)

(73) Assignee: Amorepacific Corporation, Seoul (KR)

( * ) Notice: Subject to any disclaimer, the term of this patent is extended or adjusted under 35 U.S.C. 154(b) by 360 days.

(21) Appl. No.: 12/602,421

(22) PCT Filed: May 30, 2008

(86) PCT No.: PCT/KR2008/003069
§ 371 (c)(1),
(2), (4) Date: Apr. 6, 2010

(87) PCT Pub. No.: WO2008/147148
PCT Pub. Date: Dec. 4, 2008

(65) Prior Publication Data
US 2010/0189821 A1 Jul. 29, 2010

(30) Foreign Application Priority Data

May 31, 2007 (KR) ........................ 10-2007-0053097

(51) Int. Cl.
*A61K 36/258* (2006.01)
*A23L 1/30* (2006.01)
*A61K 8/97* (2006.01)
*A61Q 19/02* (2006.01)
*A61Q 19/08* (2006.01)

(52) U.S. Cl.
CPC ............... *A23L 1/3002* (2013.01); *A61K 8/97* (2013.01); *A61K 36/258* (2013.01); *A61Q 19/02* (2013.01); *A61Q 19/08* (2013.01); *A23V 2002/00* (2013.01); *A61K 2800/522* (2013.01)
USPC ............................ 424/728; 424/401; 424/777

(58) Field of Classification Search
CPC ....... A61K 36/258; A61K 8/97; A61Q 19/08; A61Q 90/00
USPC .......................... 424/728, 777, 401
See application file for complete search history.

(56) References Cited

U.S. PATENT DOCUMENTS

| | | |
|---|---|---|
| 5,663,160 A | 9/1997 | Meybeck et al. |
| 6,238,672 B1 * | 5/2001 | Chen ............................ 424/728 |
| 2002/0012644 A1 | 1/2002 | Chen |
| 2002/0136785 A1 | 9/2002 | Yuan |

FOREIGN PATENT DOCUMENTS

| | | |
|---|---|---|
| CN | 1 170 573 A | 1/1998 |
| CN | 1 245 052 A | 2/2000 |
| DE | 20201550 U1 * | 5/2002 |
| EP | 1 327 434 A1 | 7/2003 |
| EP | 1 457 209 A1 | 9/2004 |
| EP | 1457209 | 9/2004 |
| JP | 10-072338 A | 3/1998 |
| JP | 2005-306806 * | 11/2005 |
| KR | 2004-0036111 | 4/2004 |
| KR | 10-2004-0036111 | 10/2004 |
| KR | 10-2005-0038463 | 4/2005 |
| KR | 2005-0038463 | 4/2005 |
| KR | 10-0706111 | 7/2005 |
| KR | 10-0706111 | 4/2007 |
| WO | 2006/115307 | 11/2006 |
| WO | WO 2006/115307 A1 | 11/2006 |

OTHER PUBLICATIONS

Shin (J. Ginseng Res. (2006), vol. 30, No. 3, pp. 95-99).*
Extended European Search Report in EP 08 76 6031 dated Jun. 17, 2010.
Office Action in EP 08766031 dated Feb. 10, 2011.
Anonymous, "E. Excel Elemente Natural Plants for Natural Beauty", Internet, Sep. 29, 2003, XP 002581250.
Dey et al, "Anti-hyperglycemic effects of ginseng; Comparison between root and berry", Phytomedicine (JENA), vol. 10, No. 6-7, 2003, pp. 600-605, XP 002581251.

(Continued)

*Primary Examiner* — Susan Hoffman
(74) *Attorney, Agent, or Firm* — Nixon & Vanderhye P.C.

(57) ABSTRACT

Disclosed herein is a. skin external composition containing ginseng berry extract. More specifically, disclosed is a skin external composition, which contains, as an active ingredient, ginseng berry extract having the specific components and compositions, among the above-ground parts of ginseng, and thus promotes the production of collagen in the skin, shows an MMP-I inhibitory effect and, at the same time, has skin-aging inhibitory and wrinkle-reducing effects, resulting from anti-oxidant effects and DNA damage-protecting effects. Also disclosed is a skin external composition, which contains, as an active ingredient, ginseng berry extract, which has a skin whitening effect resulting from the effects of inhibiting melanin production and reducing pigmentation caused by UV radiation, the effects of relieving dry skin symptoms and atopic symptoms by inducing and maintaining the normal differentiation of skin keratinocytes, the effect of relieving acne and skin troubles by the regulation of sebum secretion and an anti-inflammatory effect, and makes complexion ruddy through the improvement of peripheral blood circulation to make the skin clean and clear. Also disclosed is a food composition for reducing and preventing obesity, which contains, as an active ingredient, ginseng berry extract, which increases the expression of a carnitine palmitoyl transferase-1 (CPT-I) gene, serves to transport fatty acids into mitochondria in fatty acid oxidation and promotes fat oxidation.

3 Claims, 7 Drawing Sheets

(56) References Cited

OTHER PUBLICATIONS

International Search Report for PCT/KR2008/003069, mailed Sep. 29, 2008.

Attele, A.S., et al, "Antidiabetic Effects of *Panax ginseng* Berry Extract and the Identification of an Effective Component", Diabetes (2002) vol. 51, pp. 1851-1858.

Park, E.A., et al, "Insulin regulates enzyme activity, malonyl-CoA sensitivity and mRNA abundance of hepatic carnitine palmitoyltransferase-I", Biochemical Journal (1995) vol. 310, pp. 853-858.

Office Action and English language translation in KR 10-2007-0053097 dated Jul. 12, 2013.

* cited by examiner

| 2 | High-diet fat (HF) | 6 | High-diet fat (HF)+ 1.0% Red ginseng extract (RG) |
| 3 | High-diet fat (HF)+ 0.5% Ginseng berry extract (GB) | 7 | High-diet fat (HF)+ 1.5% Ginseng berry extract (GB) |
| 4 | High-diet fat (HF)+ 0.5% Red ginseng extract(RG) | 8 | High-diet fat (HF)+ 1.5% Red ginseng extract(RG) |
| 5 | High-diet fat (HF)+ 1.0% Ginseng berry extract (GB) | | |

000
COMPOSITION OF SKIN EXTERNAL APPLICATION CONTAINING GINSENG BERRY EXTRACTS

This application is the U.S. national phase of International Application No. PCT/KR2008/003069, filed 30 May 2008, which designated the U.S. and claims priority to Korean Patent Application No. 10-2007-0053097, filed 31 May 2007, the entire contents of each of which are hereby incorporated by reference.

TECHNICAL FIELD

The present invention relates to a skin external composition containing ginseng fruit (or ginseng berry) extract, and more particularly to a skin external composition, which contains, as an active ingredient, ginseng berry extract having specific components and compositions, among the aboveground parts of ginseng, and thus promotes the production of collagen in the skin, shows an MMP-1 inhibitory effect and, at the same time, has skin-aging inhibitory and wrinkle-reducing effects, resulting from antioxidant effects and DNA damage-protecting effects.

Moreover, the present invention relates to a skin external composition, which contains, as an active ingredient, ginseng berry extract, which has a skin whitening effect resulting from the effects of inhibiting melanin production and reducing pigmentation caused by UV radiation, the effects of relieving dry skin symptoms and atopic symptoms by inducing and maintaining the normal differentiation of skin keratinocytes, the effect of relieving acne and skin troubles by the regulation of sebum secretion and an anti-inflammatory effect, and makes complexion ruddy through the improvement of peripheral blood circulation to make the skin clean and clear.

In addition, the present invention provides a food composition for reducing and preventing obesity, which contains, as an active ingredient, ginseng berry extract, which increases the expression of a carnitine palmitoyl transterase-1 (CPT-1) gene, serves to transport fatty acids into mitochondria in fatty acid oxidation and promotes fat oxidation.

BACKGROUND ART

*Panax ginseng* C. A. Meyer is a plant belonging to the family Araliaceae, the genus *Panax*, and is a herbal medicine which has been used from about 2,000 years ago in Korea, China, Japan and the like in order to prevent diseases and to extend life span. The effects of ginseng, known to date, include action on the central nervous system, anti-carcinogenic action, anticancer activity, immune function regulatory action, anti-diabetic action, liver function-improving action, cardiovascular disorder-relieving and anti-atherogenic actions, blood pressure-controlling action, alleviation of menopausal disorders and osteoporosis, anti-stress and anti-fatigue actions, antioxidant activity and aging inhibitory effects (Korean Ginseng, "components and effects", the Korea Ginseng Research Institute, 56-112, 1996).

It is known that ginsenoside, which is the typical physiologically active component of ginseng, is uniformly distributed in the above-ground and underground parts of ginseng, and particularly the content and composition of ginsenoside vary depending on ginseng parts, including ginseng roots, ginseng leaves and ginseng berries (Attele A S et al, Biochem Pharmacol, 58; 1685-1693, 1999). Particularly, it was reported that the ginseng berries showed better effects than those of the ginseng roots due to the components and contents thereof different from the ginseng roots (Dey L. et al., Phytomedicine, 10; 600-605, 2003).

Recently, while the interest of consumers in natural cosmetic products has been increased, and many cosmetic products containing Chinese medicinal materials have been marketed, ginseng has also been studied as a plant material for cosmetics having important effects on the skin. However, most of such studies relate to the utilization of either extracts from ginseng roots or the ginsenosides and ginseng polysaccharides, there is no study on the effects of ginseng berry components on skin-aging inhibition and wrinkle reduction.

Also, ginseng berries have been regarded to be more valuable that ginseng and have been selectively harvested to obtain seeds. Ginseng seeds are harvested once only from 4-year-old ginseng plants during the cultivation of ginseng, and if they are harvested from 3-year, it is difficult to produce good seedlings, because the harvested seeds are too small. If the ginseng seeds are collected from 5-year old or older ginseng plants, the harvested seeds are full and good, but the development of ginseng roots is inhibited, and in addition, the tissue of the roots is not dense, and thus the quality of red ginseng prepared from the roots can be greatly deteriorated. In addition, if the ginseng seeds are harvested twice or more during ginseng cultivation, yield and red ginseng quality are greatly reduced (Korean Ginseng, "Cultivation", the Korea Ginseng Research Institute, 130-131, 1996).

U.S. Pat. No. 6,524,626 discloses a cosmetic composition containing freeze-dried ginseng berry juice and discloses that combinations of ginseng berry juice and other natural materials show the effects of moisturizing and softening the skin. However, the effects disclosed in this patent are clearly distinguished from the skin-aging inhibitory effect and wrinkle-reducing effect of the ginseng berry extract according to the present invention.

Human skin undergoes changes with age due to various intrinsic and extrinsic factors. With respect to the intrinsic factors, the secretion of various hormones regulating metabolism is reduced, and the function of immune cells and the activity of cells are reduced, thus reducing the biosynthesis of immune proteins required in vivo and bioproteins. With respect to the extrinsic factors, as the quantity of UV light that reaches the earth's surface increases due to ozone layer depletion, and environmental pollution becomes more severe, free radicals and reactive oxygen species increase, leading to various changes, including a decrease in skin thickness, an increase in wrinkles, a reduction in elasticity, the change of skin complexion to dark color, the frequent development of skin troubles, and increases in melasma, freckles and age spots.

With the progression of aging, symptoms in which the content and arrangement of skin components, such as collagen, elastin, hyaluronic acid and glycoprotein, change or decrease, occurs, and the skin undergoes oxidative stress by free radical and reactive oxygen species. It is known that, with the progression of aging or by UV light, in most cells constituting the skin, the biosynthesis of cyclooxygenase-2 (Cox-2), which produces proinflammatory cytokines known to cause inflammation, increases, the biosynthesis of matrix metalloproteinase (MMP) increases due to these inflammatory factors, and the production of nitric oxide (NO) by inducible nitric oxide synthase (iNOS) increases. That is, the biosynthesis of matrix metalloproteinase is reduced due to a decrease in cell activity, resulting from intrinsic aging, which naturally progresses, and microinflammation, degradation and degeneration are accelerated due to extrinsic factors, such as an increase in stress, resulting from various harmful environments, and an increase in reactive oxygen species, so that the skin matrix is destroyed and becomes thin, while various skin aging symptoms appear. Accordingly, many studies on active ingredients capable of preventing and relieving such aging phenomena have been conducted.

Various factors are involved in determining the human skin colors, and among them, the activity of melanocytes producing melanin pigments, the distribution of blood vessels, the thickness of the skin, and the presence or absence of pigments such as carotenoid and bilirubin in the human body, are important.

Among them, the most important factor is the black pigment melanin which is produced by the action of various enzymes such as tyrosinase in melanocytes in the human body. The production of the melanin pigment is influenced by genetic factors, physiological factors associated with hormone secretion and stress, and environmental factors such as UV radiation.

The melanin pigment, which is produced in melanocytes in the body, is a phenolic polymer in the form of a black pigment/protein composite and has useful functions to protect skin organs under the dermis by blocking UV light radiation from the sun and simultaneously to capture free radicals from the skin, thus protecting proteins and genes in the skin.

Melanin produced in the skin due to intrinsic and extrinsic stresses as described above is a stable material, which does not appear before it is discharged to the outside through skin keratinization, even when the stresses disappear. However, if melanin is produced larger than required, hyperpigmentations such as freckles and spots are induced, leading to unfavorable results in beautiful terms.

These days, women in oriental countries prefer a white and clean skin like a white gem and consider this skin as an important beauty standard. For this reason, the demand to solve therapeutic and cosmetic problems for hyperpigmentations has been increased.

To satisfy this demand, ascorbic acid, kojic acid, arbutin, hydroquinone, glutathione, their derivatives, or materials having tyrosinase inhibitory activity, have been used in cosmetics or drugs. However, the use thereof is limited due to the insufficient whitening effect thereof, a problem of skin safety, and problems of formulation and stability, which occur when they are added to cosmetic products.

The most important function of the epidermis, which is the outermost layer of the skin is to protect the skin from various external stimuli (physical and chemical stimuli, such as chemicals, pollutants, dry environments and UV light) and to prevent the excessive loss of water through the skin. This protective function can be maintained only when the stratum corneum (honey layer) consisting of keratinocytes are normally formed. The horny layer, the outermost layer of the epidermis, is formed of keratinocytes and consists of terminally differentiated keratinocytes surrounded by lipid layers (J. Invest. Dermatol., 1983; 80: 44-49). Keratinocytes are cells generated as a result of the process in which basal cells that continuously proliferate in the lowest layer of the epidermis move up toward the skin's surface while they undergo a series of structural and functional changes. After a given period, old keratinocytes are shed from the skin and replaced by new keratinocytes. This repeated process is called "differentiation of epidermal cells" or "keratinization". During the keratinization process, keratinocytes form the horny layer, while they produce natural moisturizing factor (NMFs) and intracellular lipids (ceramide, cholesterol and fatty acid), such that the horny layer has firmness and softness to function as a skin barrier.

However, this horny layer can easily lose its functions due to lifestyle factors such as excessive face washing or bathing, environmental factors such as dry atmospheres or pollutants, and intrinsic diseases such as atopic skin or senile skin. In fact, due to various factors which recently increased, persons suffering from dry skin symptoms and various disorders caused thereby gradually increase. Thus, to maintain skin water at a suitable level, many studies focused on supplying external water or preventing the loss of water from the body have been conducted. In fact, various kinds having moisturizers having water retention capability have been developed and mainly used in the cosmetic field.

However, as factors harmful to humans in life environment gradually increase and an aged population rapidly increases, the turnover rate of the horny layer becomes slow, and the lipid synthesis capability of keratinocytes is reduced, or the division, growth and differentiation of cells in the epidermis are not smooth. Thus, humans having skins, in which the amount of moisturizing factors and lipids is reduced such that the function of the horny layer is not maintained (i.e., the skin barrier function is not maintained), gradually increase.

Due to the abnormal division and differentiation of epidermal cells, various skin diseases, including xerosis cutis, atopy and psoriasis, occur. Such diseases can be slightly relieved with conventional moisturizers only having water retention capability, but it is difficult to expect the fundamental cure of the diseases.

In skins including scalps and faces, sebum geneally functions to maintain skin moisturization or to prevent the invasion of microorganisms. However, if sebum is excessively secreted, the falling out of hair is stimulated, acne worsens, the enlargement of follicles is promoted, and seborrhoic dermatitis occurs.

This excessive sebum secretion is caused by various factors, and with respect to the most important factor, sebaceous gland cells are activated by the amount of dihydrotestosterone (DHT), which is a hormone involved in promoting sebum secretion, thus excessively secreting sebum. That is, in the loss of hair, testosterone (T) is converted into dihydrotestosteron by 5-α-reductase type 2 in cells and, at the same time, binds to a receptor in the cytoplasm and enters the nuclei, thus causing the loss of hair. However, in the skin or sebaceous gland, testosterone is converted into dihydrotestosteron by 5-α-reductase type 1 to activate sebaceous gland cells and to stimulate the differentiation of the cells, and thus serum in the sebaceous gland is excessively secreted, thus causing acne (J. Invest Dermatol 105:209-214 Diane etc).

In addition to the simple excessive secretion of sebum, skin troubles such as acne and hair loss worsen by fine inflammatory reactions on the skin. In the process of development of acne, excessive sebum is accumulated in hair follicles to activate *Propionibacterium acnes* and to cause inflammation.

Because the ginseng berry extract according to the present invention has anti-inflammatory effects together with excellent antioxidant effects, it inhibits the production of prostaglandins, particularly prostaglandin (PGE2), in cellular inflammatory reactions, and inhibits the production of the proinflammatory factor NO (nitric oxide) by iNOS, thus relieving skin troubles, such as acne, resulting from the excessive secretion of sebum.

However, such natural materials, which are safe for the skin, fundamentally reduce the secretion of sebum and, at the same time, relieve inflammatory action, are not abundant.

Meanwhile, obesity refers to a condition in which energy intake and consumption are kept in balance due to genetic factors or lifestyle factors, and excess energy is accumulated as fat to cause abnormally increase body fat and to cause abnormal metabolism. Obesity is a serious health problem not only in Western Europe, in which meat is the principle food, but also in Korea, and it handicaps individuals in social or mental terms and, in addition, acts as a major factor of increasing the risk of hypertension, hyperlipidemia, arteriosclerosis, heart disease, diabetics and the like. It is known that 30-40% of modern persons have obesity, and in advanced countries, 2-7% of total health expenditures are attributable to overweight and obesity. In Korea, the socioeconomic cost of obesity inside and outside the health care system was about 1,001,700,000,000 Won (Korean currency) in the year 1998 and increased to about 1,800,000,000,000 Won (Korean currency). If the current rate of increase in obesity is maintained, the socioeconomic cost of obesity is expected to increase continuously.

According to data from the 2005 Korean National Health and Nutrition Survey, the prevalence of obesity (more than 20 years old) was 31.8% in total, 35.2% in men and 28.3% in women. It increased compared to data in the years 1998 and 2001, and it is considered that this increase is mainly attributable to the westernization of eating habits (the ratio of fatty energy accounts for more than 20%), an increase in alcoholic consumption, a change in lifestyle, such as the skipping of breakfast, etc. (Korea Food and Drug Administration, 2005 Korean National Health and Nutrition Survey, Nutrition Survey, "What, how much and how Korean eat their food?").

Various methods for treating and preventing obesity have been actively studied in various countries and include diet therapies of reducing energy consumption by inhibiting food intake ((dietary restriction therapy, low-energy diet therapy, very low-energy diet therapy, and fasting therapy), exercise therapy of consuming energy through exercise, psychotherapies (Behavior Modification Therapy and cognitive-behavior therapy), drug therapies which use a energy metabolism promoter, an appetite suppressant, a digestion and absorption suppressant and the like, and surgical therapies such as the partial excision of organs or liposuction. Among them, the diet therapy and exercise therapy are fundamental methods for the treatment of obesity. Also, in the diet therapy of obesity, it is considered preferable that low-energy diet be used, protein requirement be ensured, lipids be minimized, and the remainder be carbohydrate, and preferably low-GI carbohydrate.

The frequency of prior patent applications relating to obesity is in the order of inventions for inhibiting the absorption of saccharides (regulation of digestion), inventions for regulating the metabolism of body fat accumulated in the body (inhibition of body fat), inventions for inhibiting the absorption of fat, and inventions for controlling appetite. Among them, an example of the invention for inhibiting the absorption of saccharides (regulation of digestion) is PCT International Application No. PCT/US01/31860, entitled "GINSENG BERRY EXTRACTS AND PHARMACEUTICAL COMPOSITIONS FROM GINSENG BERRY FOR THE TREATMENT OF TYPE 2 DIABETES AND OBESITY". However, the method for inhibiting the absorption of saccharides has a problem in that, it is discontinued, the yo-yo phenomenon that body weight increases again occurs. Thus, there is an urgent need to develop a method for promoting a reduction in body weight.

Accordingly, in view of various diseases resulting from obesity, it is evident that a decrease in fat body is more important than a simple decrease in body weight. When it is considered preferable to find a method capable of reducing the accumulation of ingested fat and activating fat oxidation, the investigation of a method capable of increasing the beta-oxidation of fatty acid can be an excellent target for the treatment of obesity. Particularly, the metabolism of fatty acid can be promoted by regulating the expression of CPT-1, which is a major enzyme determining the beta-oxidation rate of fatty acid (McCarty, Medical Hypotheses 57(3): 324-336, 2001).

Thus, there has been a need to develop a novel neutral material, which has an excellent effect of reducing body fat and is also effective in reducing body weight.

DISCLOSURE

Technical Problem

Accordingly, the present inventors have studied a cosmetic product, having an effect on the skin, using ginseng berries which are the above-ground parts of ginseng, and, as a result, have found that an extract from ginseng berries has an effect on the skin due to the components and compositions different from those of general ginseng and red ginseng, thereby completing the present invention.

In addition, the present inventors have studied to find a natural material, which increases the expression of a CPT-1 gene, which is an enzyme determining the oxidation rate of fatty acid, using ginseng berries which are the above-ground parts of ginseng, in addition to using ginseng roots which are the underground parts of ginseng, and, as a result, have found that an extract from ginseng berries has an effect of reducing body fat due to the components and compositions different from those of general ginseng and red ginseng, thereby completing the present invention.

Therefore, it is an object of the present invention to prepare ginseng berry extract, having an antioxidant effect, a collagen production-promoting effect and an MMP-1 inhibitory effect, from ginseng berries, and to provide a skin external composition for inhibiting skin aging and reducing skin wrinkles, which contains the prepared extract as an active ingredient.

Another object of the present invention is to provide a skin external composition for skin whitening, which contains the ginseng berry extract as an active ingredient, and thus shows a skin whitening effect through the inhibition of melanin production and the reduction of pigmentation.

Still another object of the present invention is to provide a skin external composition for moisturizing the skin or relieving atopic symptoms, which contains the ginseng berry extract as an active ingredient, and thus has the effects of moisturizing the skin and relieving atopic symptoms by inducing and maintaining the normal differentiation of epidermal keratinocytes.

Still another object of the present invention is to provide a skin external composition for anti-inflammation, which contains the ginseng berry extract as an active ingredient, and thus can relieve skin troubles, including acne, by showing a sebum regulatory effect and an anti-inflammatory effect, that is, by inhibiting the production of inflammatory factors.

Still another object of the present invention is to provide a skin external composition for improving skin complexion, which contains the ginseng berry extract as an active ingredient, and thus shows effects of skin vasodilation and blood circulation improvement and makes the skin clean and clear.

Yet another object of the present invention is to provide a health functional food composition, which can increase the expression of a CPT-1 gene, which is an enzyme determining the oxidation rate of fat, to stimulate the degradation metabolism of body fat and prevent and reduce obesity.

Technical Solution

To achieve the above objects, in one aspect, the present invention provides a skin external composition for inhibiting skin aging and reducing wrinkles, which contains ginseng berry extract as an active ingredient.

In another aspect, the present invention provides a skin external composition for skin whitening, which contains the ginseng berry extract as an active ingredient, and thus a skin whitening effect through the inhibition of melanin production and the reduction of pigmentation.

In still another aspect, the present invention provides a skin external composition for moisturizing the skin and relieving atopic symptoms, which contains the ginseng berry extract as an active ingredient, and thus shows the effects of moisturizing the skin and relieving atopic symptoms by maintaining the normal differentiation of epidermal keratinocytes.

In still another aspect, the present invention provides a skin external composition for anti-inflammation, which contains the ginseng berry extract as an active ingredient, and thus has the effect of regulating sebum and the effect of relieving acne and skin troubles through the regulation of inflammatory reactions.

In still another aspect, the present invention provides a skin external composition for improving skin complexion, which contains the ginseng berry extract as an active ingredient, and thus stimulates peripheral blood circulation to improve skin blood flow, thus making skin complexion ruddy.

In still another aspect, the present invention provides a food composition for preventing and reducing obesity, which contains the ginseng berry extract as an active ingredient.

In yet another aspect, the present invention provides a food composition for promoting the degradation of neutral fat in adipose cells, which contains the ginseng berry extract as an active ingredient.

Advantageous Effects

According to the present invention, there can be provided a skin external composition, which contains, as an active ingredient, ginseng berry extract having the components and compositions different from those of ginseng roots, and thus has the effects of inhibiting skin aging, reducing skin wrinkles, whitening the skin, moisturizing the skin, relieving atopic symptoms and relieving acne and skin troubles.

In addition, a food composition for preventing and reducing obesity according to the present invention increases the expression of the L-carnitine palmitoyl-transferase (CPT-1) gene, which is the key enzyme of the fatty acid degradation pathway, and it functions to transport fatty acid into mitochondria in fatty acid oxidation and promotes the oxidation of fatty acid. Thus, it has excellent effects of inhibiting and preventing obesity.

BEST MODE

Figure 1:
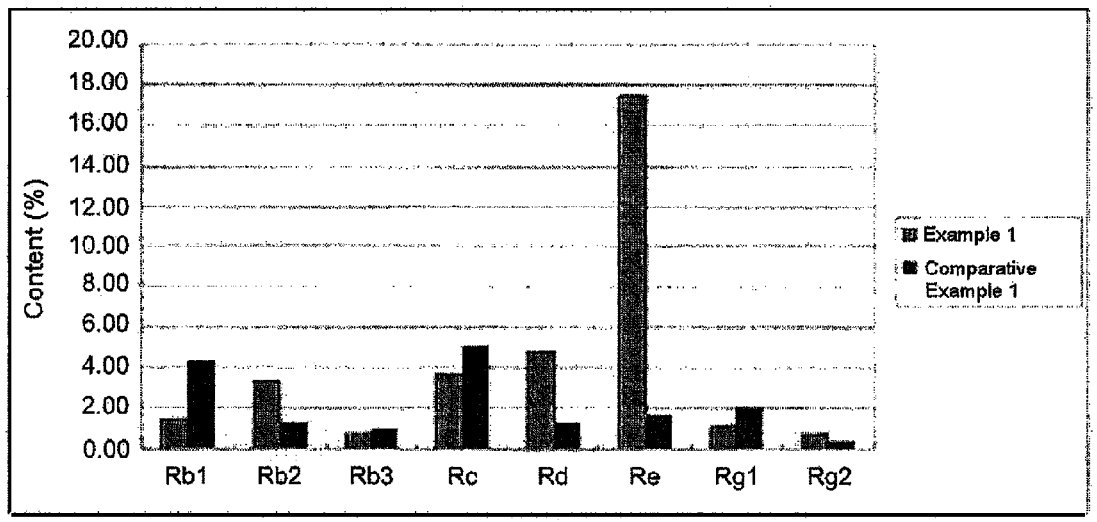
FIG. 1 is a graphic diagram showing analysis results for the ginsenosides of ginseng berry extract of Example 1 and a ginseng extract of Comparative Example 1.

Hereinafter, the present invention will be described in further detail.

The ginseng berry extract that is used in the present invention is prepared by drying the fresh and skin of ginseng berries, from which the seeds have been removed, in sunlight or hot air, and then extracting the dried material with water or ethanol. Specifically, the ginseng berry extract can be prepared through, but not limited to, the following steps:

1) drying the fresh and skin of ginseng berries; and 2) adding water or ethanol to the dried material of step 1), extracting the solution under reflux, filtering the extract and concentrating the filtrate under reduced pressure.

In the present invention, the ginseng berry extract can be added in an amount of 0.001-50 wt % based on the total weight of the skin external composition depending on the formulation of the skin external composition. Preferably, the ginseng berry extract is added in an amount of more than 0.001 wt % in view of its effects, and it is added in an amount of more than 50 wt % in consideration of the formulation of the skin external composition.

The cosmetic composition according to the present invention contains a cosmetically or dermatologically acceptable medium or base. It can be provided in the form of all formulations suitable for topical application, for example, solutions, gels, solids, pastes, emulsions obtained by dispersing an oily phase in an aqueous phase, suspensions, microemulsions, microcapsules or microgranules, the form of ionic (liposome) and non-ionic dispersions or the form of cream, skin lotion, powder, ointment, powder, spray or stick. These compositions may be prepared according to any conventional method known in the art. The composition according to the present invention can also be used in the form of foam or the form of an aerosol composition further containing a compressed propellant.

The cosmetic composition of the present invention may contain additives, which are conventionally used in the cosmetic or dermatological field, including fatty materials, organic solvents, solubilizing agents, concentrating agents, gelling agents, softening agents, antioxidants, suspending agents, stabilizing agents, foaming agents, aromatic agents, surfactants, water, ionic or non-ionic emulsifiers, fillers, sequestering agents, chelating agents, preservatives, vitamins, blocking agents, wetting agents, essential oil, dyes, pigments, hydrophilic or lipophilic activators, lipid vesicles, or other components which are conventionally used in cosmetic products. The additives are introduced in an amount which is generally used in the cosmetic or dermatological field.

There is no particular formulation on the formulation of the inventive skin external composition containing the ginseng berry extract, and the composition can be formulated into cosmetic products, for example, skin lotion, astringent lotion, milk lotion, nourishing cream, massage cream, essence, eye cream, eye essence, cleansing cream, cleansing foam, cleansing water, pack, powder, body lotion, body cream, body oil and body essence.

Obesity occurs due to the accumulation of non-consumed calorie resulting from the imbalance of ingested nutrients, a decrease in lipolytic ability by intestinal enzymes resulting from the imbalance of energy metabolism, a decrease in the secretion of leptin, which is a body fat degradation enzyme, the deficiency of adrenergic receptor, which involved in the oxidation of fat accumulated in the body, and the accumulation of body fat resulting from genetic factors and constitution.

Fatty acid, which is the structural component of fat, enters cells, in which it undergoes beta-oxidation, TCA cycle and oxidative phosphorylation, produces ATP using a large amount of oxygen and becomes a form that is easily used as energy. However, because fatty acid is a large molecule, it cannot pass through the mitochondria membrane. Long-chain fatty acid, which enters the cytosol in blood, cannot pass through the mitochondrial membrane, but it can enter mitochondria, when it is subjected to the following three serial enzymatic reactions:

(1) long-chain fatty acid present in the cytosol forms a thiol ester linkage between the fatty acid carboxyl group and the thiol group of coenzyme A by acyl-CoA synthetase present in the outer mitochondrial membrane. The produced fatty acyl-CoA has the properties of high energy compounds as does acetyl-CoA.

(2) The fatty acyl-CoA ester formed in the outer mitochondrial membrane cannot pass through the inner mitochondrial membrane. To transport fatty acid into mitochondria, CPT-1 present on the outer surface of the inner mitochondria membrane catalyzes the transesterification of the fatty acyl group from Co-A into carnitine. The produced fatty acyl-carnitine ester crosses the inner mitochondrial membrane into the matrix by facilitated diffusion through the acyl-carnitine/carnitine transporter.

(3) The fatty acyl-carnitine is converted into fatty acyl-CoA by carnitine acyltransferase II.

The fatty acid, entered through the three steps, is converted into acetyl-CoA by beta-oxidation, and the acetyl-CoA is converted into the final products electrons and $CO_2$, in which the produced electrons produce ATP through a respiratory chain process (Lehninger et al., Principles of Biochemistry: 479-505, 1993).

The ginseng berry extract that is used in the present invention functions to increase the expression of the CTP-1 gene in order to promote the fat oxidation metabolism.

The inventive food composition for preventing and reducing obesity may contain the ginseng berry extract in an amount of 0.01-100 wt % based on the total weight of the composition depending on the formulation of the composition.

The inventive food composition for preventing and reducing obesity, which contains the ginseng berry extract, increases the expression of the carnitine palmitoyl transferase-1 (CPT-1) gene acting as a key enzyme in the fatty acid degradation pathway.

Also, the inventive food composition containing the ginseng berry extract functions to transport fatty acid into mitochondria in fatty acid oxidation and promotes the oxidation of neutral fat.

MODE FOR INVENTION

Hereinafter, the construction and effect of the present invention will be described in further detail with reference to examples and Experimental Examples. It is to be understood, however, that these examples and Experimental Examples are illustrative only, and the scope of the present invention is not limited thereto.

Example 1

Preparation of Ginseng Berry Extract

1) Pretreatment of Ginseng Berry
Raw ginseng berries were harvested, and the seeds were separated and removed therefrom. Then, the fresh and skin of the ginseng berries were dried in sunlight or hot air, thus preparing the dried ginseng berry material.
2) Preparation of Ginseng Berry Extract
1 kg of the dried ginseng berry was added to 3 L of water and extracted under reflux. Then, the extract was filtered, and then concentrated at 40-45° C. under reduced pressure, thus obtaining 300 g of ginseng berry extract.

Comparative Example 1

Preparation of Ginseng Root Extract

Ginseng root extract was prepared in the same manner as in Example 1, except that the same amount of ginseng roots were used instead of the ginseng berries.

Comparative Example 2

Preparation of White Ginseng Extract

White ginseng extract was prepared in order to compare the effect thereof with that of the ginseng berry extract. 1 kg of white ginseng or white ginseng powder was added to 3 L of water or alcohol and extracted three times under reflux. Then, the extract was filtered according to a conventional method and concentrated under reduced pressure, thus obtaining about 250 g of white ginseng extract.

Comparative Example 3

Preparation of Red Ginseng Extract

Red ginseng extract was prepared in order to compare the effect thereof with that of the ginseng berry extract. 1 kg of red ginseng (water content: 14%) or red ginseng powder was added to 3 L of water or alcohol and extracted three times under reflux. The extract was filtered according to a conventional method, and then concentrated under reduced pressure, thus obtaining about 250 g of red ginseng extract.

Experimental Example 1

Comparison of Components of Ginseng Berry Extract

<Analysis of Ginsenosides (*Ginseng saponins*) of Ginseng Berries and Ginseng Roots>
The ginseng berry extract and the ginseng root extract was prepared in Examples 1 and Comparative Example 2, respectively. These extracts were treated with ether to remove oil-soluble components, and then crude saponins were extracted with butanol (BuOH) and concentrated. The ginsenosides of the concentrated materials were analyzed through HPLC, and the analysis results are shown in FIG. 1 and Table 1.

TABLE 1

|  | Example 1 | Comparative Example 1 |
| --- | --- | --- |
| Crude saponin content (dry weight) | 33.42% | 16.70% |
| PD/PT ratio | 0.73 | 3.23 |

The ginseng berry extract prepared in Example 1 had a crude saponin content about 2-fold higher than that of the ginseng root extract prepared in Comparative Example 1. When the ginsenosides were divided into the PD (protopanaxadiol) class—"ginsenosides Rb1, Rb2, Rc and Rd", and the PT (protopanaxatriol) class—"ginsenosides Re, Rg1 and Rb2", the PD/PT ratios of the extracts were 0.73 and 3.23, respectively, suggesting that the ginseng berry extract and the ginseng root extract were distinctly different from each other with respect to their compositions.

<Analysis of Mineral Components of Ginseng Berry Extract>

In order to examine whether the ginseng berry extract prepared in Example 1 has the characteristics of berries unlike ginseng, the analysis of minerals including vitamins was carried out. The analysis results are shown in Table 2.

TABLE 2

| Components | Contents | Components | Contents |
| --- | --- | --- | --- |
| Potassium (mg/100 g) | 5865.57 | Magnesium (mg/100 g) | 354.38 |
| Calcium (mg/100 g) | 819.26 | Zinc (mg/100 g) | 178.49 |
| Iron (mg/100 g) | 59.31 | Vitamin A (μg/100 g, RE) | 213.11 |
| Phosphorus (mg/100 g) | 187.17 | Vitamin B1(mg/100 g) | 12.29 |
| Vitamin B2 (mg/100 g) | 8.45 | Vitamin B6 (mg/100 g) | 10.50 |
| Vitamin C (mg/100 g) | 4.91 | Vitamin E (mg/100 g, α-TE) | 23.61 |
| Vitamin K (μg/100 g) | 232.12 | Niacin (mg/100 g, NE) | 5.76 |
| Pantothenic acid (mg/100 g) | 5.87 | Folic acid (μg/100 g) | 349.97 |

As described above, it could be seen that the ginseng berry extract that is used in the present invention contained ginseng saponins in an amount larger than that in the ginseng root extract, and the properties of the saponins thereof were contrary to each other. Also, it could be found that the ginseng berry extract was rich in the contents of vitamins and 16 minerals compared to the root ginseng extract. Based on these results, the following tests were carried out to examine the effects of the ginseng berry extract on the skin.

Experimental Example 2

Effects of Inhibiting Skin Aging and Reducing Skin Wrinkles

1) Antioxidant Effect of Ginseng Berry Extract

Figure 2:
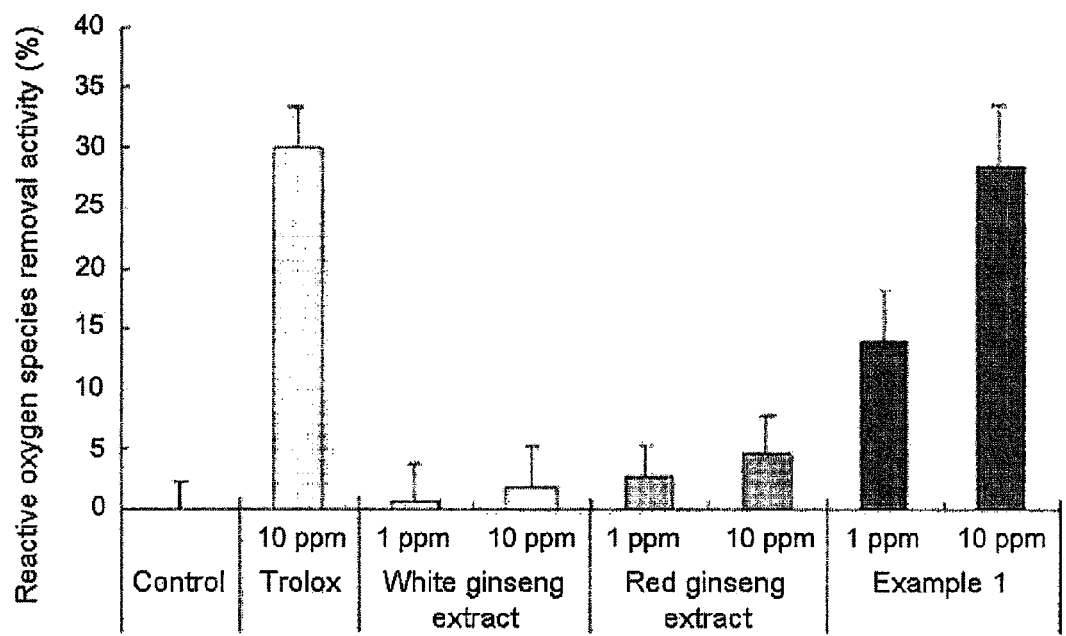
FIG. 2 is a graphic diagram showing the reactive oxygen species removal activities of test materials.

The antioxidant effect of the ginseng berry extract was examined by comparing the abilities to remove reactive oxygen species (ROS), which were generated by UV radiation. As a positive control group, trolox, which is generally used for the comparison of antioxidant effects, was used, and it was compared with white ginseng extract and red ginseng extract (FIG. 2). Also, a group not treated with the test material was used as a control group.

In the results shown in FIG. 2, the ginseng berry extract of Example 1 of the present invention showed the effect of significantly removing reactive oxygen species, produced by UV radiation, compared to the control group, in a human HaCaT keratinocytes monolayer culture system. This activity is an excellent activity similar to that of trolox, used as the index of the activity of antioxidant substances, and makes a contrast with the white and red ginseng extracts having no significant removal activity. Specifically, it was found that the ginseng berry extract prepared in Example 1 of the present invention 1 had the effects of preventing wrinkle formation, a decrease in elasticity and pigmentation by significantly removing reactive oxygen species resulting in skin aging.

2) Analysis of Inhibitory Activity Against Oxidative Damage to DNA by Single Cell Gel Electrophoresis (SCGE, Comet Assay)

Human normal fibroblasts were cultured for 24 hr and treated with varying concentrations of each of the ginseng berry extract of Example 1 and vitamin E. After 12 hr, the cells were treated with the positive control $H_2O_2$ (final concentration: $10^{-3}$M), and then stained by electrophoresis. The stained cells were observed with a fluorescent microscope. Herein, the image analyzer KOMET 3.1 (Kinetic Imaging, England) was used to analyze the tail length (μm) resulting from the digestion of DNA in each of 25 cells, and the analysis results are shown in Table 3 below.

TABLE 3

| Inhibitory action of ginseng berry extract and vitamin E against oxidative damage to DNA | | |
| --- | --- | --- |
| Test materials | Tail length (μm) | Inhibition (%) |
| $H_2O_2$ | 115.6 | — |
| $H_2O_2$ + Example 1 (10 ppm) | 75.8 | 34.4 |
| $H_2O_2$ + Example 1 (50 ppm) | 65.7 | 43.2 |
| $H_2O_2$ + Example 1 (100 ppm) | 52.1 | 54.9 |
| $H_2O_2$ + vitamin E (10 ppm) | 70.6 | 38.9 |

In the results shown in Table 3, the results of the cell gel electrophoresis showed that the ginseng berry extract of Example had significant inhibitory activity against oxidative damage to DNA, suggesting that the ginseng berry extract according to the present invention can act as an inhibitor of oxidative DNA damage, which inhibits single strand break caused by a hydroxyl radical (—OH).

3) Type I Procollagen Assay

Human fibroblasts were cultured in a 12-well culture plate at a concentration of $10^5$ cells/well, and then the medium was replaced with media containing 1 ppm and 10 ppm of the ginseng berry extract of Example 1. At 3 days of culture, the cells were harvested, and the amount of the produced type I procollagen was quantified using an ELISA method. The measurement results were calculated relative to 100 for the control group not containing the ginseng berry extract of Example 1, and TGF-b was used as a positive control group. Also, the measurement results were compared with those of the white ginseng root and red ginseng root extracts.

Figure 3:
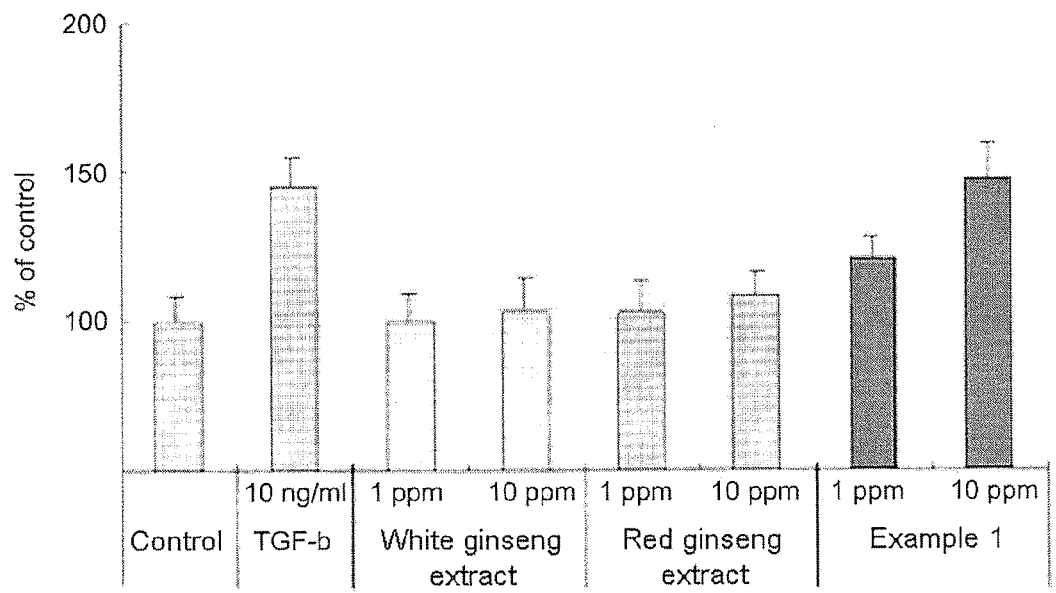
FIG. 3 is a graphic diagram showing measurement results for the collagen production of the ginseng berry extract of Example 1.

In the normal human fibroblast monolayer culture system, the ginseng berry extract of Example 1 showed the effect of significantly promoting the production of type I procollagen compared to the control group. That is, the ginseng berry extract of Example 1 could inhibit a decrease in collagen production resulting from human skin aging and showed the effect of reducing skin wrinkles (FIG. 3).

4) Analysis of Inhibition of MMP-1 Expression

Human fibroblasts were cultured in a 12-well culture plate at a concentration of $10^5$ cells/well, and then radiated with 40 mJ/cm$^2$ of UVB. Then, the culture medium was replaced with media containing 1 ppm and 10 ppm of the ginseng berry extract of Example 1. At 2 days of culture, the cells were harvested, and the amount of the produced MMP-1 (matrix metalloproteinase I) was quantified using an ELISA method. The measurement results were calculated relative to 100 for a UV control group not containing the test material, and TGF-b was used as a positive control group. Also, the measurement results were compared with the white ginseng root and red ginseng root extracts.

Figure 4:
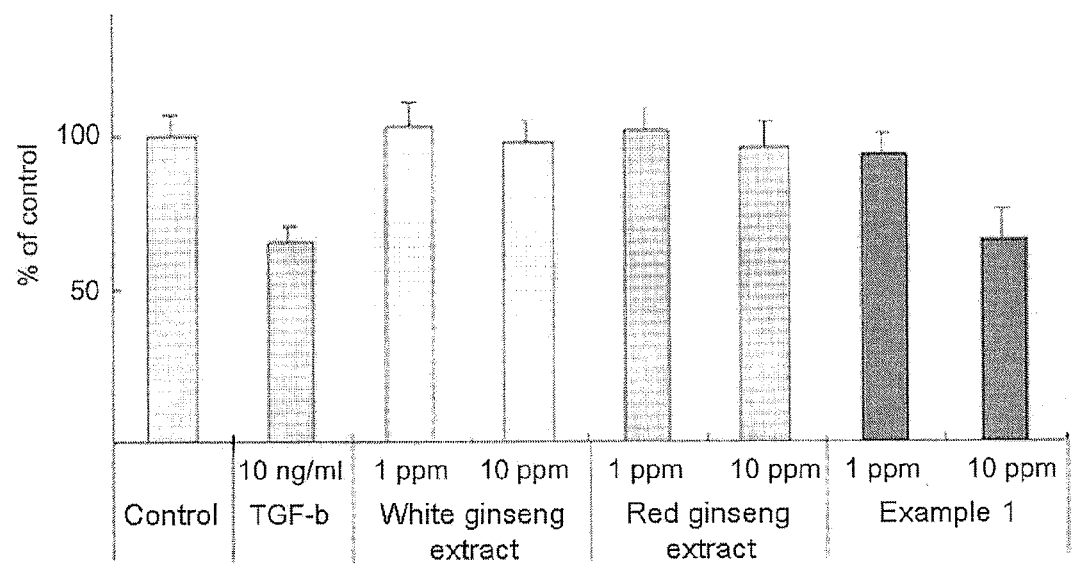
FIG. 4 is a graphic diagram showing measurement results for the MMP-1 biosynthesis inhibitory effect of the ginseng berry extract of Example 1.

In the normal human fibroblast monolayer culture system, the ginseng berry extract of Example 1 of the present invention significantly inhibited the expression of MMP-1 induced by 40 mJ/cm$^2$ of UVB. This suggests that the ginseng berry extract of Example 1 of the present invention has effects on the inhibition of skin aging and the reduction of wrinkles by inhibiting the biosynthesis of the skin tissue degradation enzyme MMP-1 resulting from intrinsic aging or external environmental factors (FIG. 4).

5) Inhibitory Effect Against Cyclooxygenase-2 (COX-2) Biosynthesis Resulting from UV Radiation Human fibroblasts were cultured in a 12-well culture plate at a concentration of $10^5$ cells, and then radiated with 15 J/cm$^2$ of UVA. Then, the culture medium was replaced with a medium containing 0.1 ppm, 1 ppm and 10 ppm of each of the ginseng berry extract of Example 1 and the ginseng root extract of Comparative Example 1. At 2 days of culture, the cells were harvested, and the amount of the produced cyclooxygenase-2 (COX-2) was densitometrically quantified using a Western blot method. The measurement results were calculated relative to 100 for a UV control group not containing the test material. The measurement results are shown in Table 4 below.

TABLE 4

| Test material concentration (ppm) | | COX-2 biosynthesis (%) |
|---|---|---|
| Example 1 | 10 | 11 |
| | 1 | 38 |
| | 0.1 | 63 |
| Comparative Example 1 | 10 | 72 |
| | 1 | 91 |
| | 0.1 | 99 |
| Control group | | 100 |

From the results of Table 4 above, it could be seen that the ginseng berry extract of Example 1 concentration-dependently reduced the synthesis of cyclooxygenase-2 resulting from UV radiation and prevented skin tissue degradation caused by the COX-2 product prostaglandin E2 (PGE2).

6) Inhibitory Effect Against Biosynthesis of Tumor Necrosis Factor-α (TNF-α)

Human keratinocytes were cultured in a 12-well culture plate at a concentration of $10^5$ cells/well, and then radiated with 30 mJ/cm$^2$ of UVB. Then, the culture medium was replaced with media containing 0.1 ppm, 1 ppm and 10 ppm of each of the ginseng berry extract of Example 1 and the ginseng root extract of Comparative Example 1. After 6-24 hours of culture, the cells were harvested, and the amount of the produced tumor necrosis factor-α (TNF-α) was quantified using an ELISA (Pharmingen 555212) method. The measurement results were calculated relative to 100 for a UV control group not treated with the test material. The calculation results are shown in Table 5 below.

TABLE 5

| Test material concentration (ppm) | | TNF-α biosynthesis |
|---|---|---|
| Example 1 | 10 | 16 |
| | 1 | 38 |
| | 0.1 | 72 |
| Comparative Example 1 | 10 | 74 |
| | 1 | 85 |
| | 0.1 | 92 |
| Control group | | 100 |

From the results of Table 5, it was found that the ginseng berry extract of Example 1 of the present invention concentration-dependently reduced the biosynthesis of tumor necrosis factor-α (TNF-α) caused by UV radiation, and thus could prevent skin aging resulting from the biosynthesis of (TNF-α).

7) Effect of Reducing Human Skin Wrinkles

Nourishing cream of Example 2, having the composition shown in Table 6 and containing the ginseng berry extract of Example 1, and nourishing cream of Comparative Example 2, not containing the ginseng berry extract, were prepared. The prepared creams were applied to forty 30-50-year-old test subjects, and the effects of the creams on the reduction of skin wrinkles were comparatively evaluated (unit: wt %).

TABLE 6

| Components | Example 2 | Comparative Example 2 |
|---|---|---|
| Ginseng berry extract | 0.1 | — |
| Beeswax | 10 | 10 |
| Polysorbate 60 | 1.5 | 1.5 |
| PEG 60 hydrogenated castor oil | 2 | 2 |
| Sorbitan sesquioleate | 0.5 | 0.5 |
| Liquid paraffin | 10 | 10 |
| Squalane | 5 | 5 |
| Capylic/capric triglyceride (Estasan: Uniqema) | 5 | 5 |
| Glycerin | 5 | 5 |
| Butyleneglycol | 3 | 3 |
| Propyleneglycol | 3 | 3 |
| Triethanolamine | 0.2 | 0.2 |
| Preservative, pigment and fragrance | q.s. | q.s. |
| Purified water | Balance | Balance |

Example 2 was applied on the left side of the face of the subjects for 3 months, and Comparative Example 3 was applied on the right side for 3 months. The conditions of both sides of the face were measured before application of the creams, and after 3-month application of the creams, the conditions of the same portions were measured again, thus measuring changes in skin wrinkles. In a constant-temperature and constant-humidity chamber at a temperature of 24° C. and a relative humidity of 40%, wrinkles at the outer corner of the eyes were reproduced with a replica, and the facial wrinkles were measured with a Visiometer system (C+K Inc.). The change in skin wrinkles was calculated according to the following equation 1.

$$\text{Change}(\Delta\%)=(Tdi-Tdo)/Tdo\times 100 \quad \text{[Equation 1]}$$

wherein "Tdi" is a value measured at D90, and "Tdo" is a value measured at D0.

In the results of calculation according to the equation 1, the skin wrinkles at the portion applied with Comparative Example 2 showed a decrease of 6.5±4% (mean±standard deviation), whereas the skin wrinkles at the portion applied with Example 2 showed a decrease of 39±11%, suggesting that Example 2 showed an excellent effect of reducing skin wrinkles.

8) Effect of Improving Skin Elasticity in Human Body

The skin elasticity improvement effects of Example 2 and Comparative Example 1, having the compositions shown in Table 6, were measured.

40 women, 30 years old or more, were divided into 2 groups. The faces of the subjects in each of the groups were applied with the nourishing creams of Example 2 and Comparative Example 2 two times every day for 12 weeks, and then the skin elasticity of the faces was measured using Cutometer SEM 575 (C+K Electronic Co., Germany). The measurement results are shown in Table 7 below. The results in Table 7 indicate viscoelasticity measured by the Cutometer.

TABLE 7

| Test material | Skin elasticity effect |
| --- | --- |
| Example 2 | 0.46 ± 0.12 |
| Comparative Example 2 | 0.29 ± 0.09 |

As can be seen from the results of Table 7, the application of the nourishing cream of Example 2 containing the ginseng berry extract of Example 1 showed a skin elasticity improvement effect of about 150%.

Experimental Example 3

Skin Whitening Effect

1) Analysis of Melanin Production Inhibitory Effect Using Mouse Melanocytes

Mouse melanocytes were used to examine the melanin production inhibitory effect of the ginseng berry extract of Example 1.

First, C57BL/6 mouse melanocytes (Mel-Ab cells) (Dooley, T. P. et al, Skin pharmacol, 7, pp 188-200) were cultured in DMEM (Dulbeccos modified Eagles media), containing 10% fetal bovine serum, 100 nM 2-O-tetradecanoyphorbol-13-acetate and 1 nM cholera toxin, in conditions of 37° C. and 5% $CO_2$. The cultured Mel-Ab cells were detached with 0.25% trypsin-EDTA and cultured in a 24-well culture plate at a concentration of $10^5$ cells/well. Then, from 2 days of culture, each of 1 ppm and 10 ppm of the ginseng berry extract was continuously added thereto and cultured for 3 days. Herein, the red ginseng extract and hydroquinone were used as positive control groups. Then, the culture media were removed, and the cells were washed with PBS and lysed with sodium hydroxide. The lysed cells were measured for absorbance at 400 nm, and then the inhibition of melanin production was calculated according to the following equation 2. The calculation results are shown in Table 8 (Dooley's method).

$$\text{Inhibition}(\%) \text{ of melanin production}=100-(\text{absorbance of each test material/absorbance of control}\times 100) \quad \text{[Equation 2]}$$

TABLE 8

| Test material | Melanin production inhibition (%) |
| --- | --- |
| Example 1 (1 ppm) | 14.0 |
| Example 1 (10 ppm) | 34.4 |
| Red ginseng extract (10 ppm) | 5.3 |
| Hydroquinone (control) | 41.1 |

As shown in Table 8 above, it was found that the ginseng berry extract of Example 1 of the present invention showed a melanin production inhibition rate, which was higher than that of the red ginseng extract and similar to that of hydroquinone. This suggests that the ginseng berry extract of Example 1 of the present invention showed an excellent whitening effect.

2) Whitening Effect on Human Skin

In order to examine the whitening effect of the ginseng berry extract of Example 1 on the human skin, the following test was carried out.

First, on 12 healthy men, a 1.5-cm perforated opaque tape was attached to the upper arm portion of the subjects, and then the attached portion was radiated with UVB at a dose about 1.5-2 times the minimal erythema dose of each subject to induce skin darkening.

After the UV radiation, each of the ginseng berry extract (test material) of Example 1 and hydroquinone was applied on the UV-radiated portion, and a change in the state of the applied portion was observed for 10 weeks in comparison with a control portion not applied with anything. The color of the skin was measured with the colorimeter CR2002 (Japan, Minolta) at 1-week intervals.

Then, the difference ($\Delta L^*$) in skin color between the time point of initiation of application and the time point of completion of application of each test material was calculated according to the following equation 3, and the calculation results are shown in Table 9 below. Meanwhile, the whitening effect is evaluated by measuring the $\Delta L^*$ value between the sample-applied portion and the control portion. A $\Delta L^*$ value of about 2 indicates that pigmentation is clearly relieved, and if it is more than about 1.5, it can be judged to have a whitening effect.

$$\Delta L^*=L^*\text{value at the time of completion of application}-L^*\text{value at the time of initiation of application} \quad \text{[Equation 3]}$$

TABLE 9

| Test materials | Skin-color brightness ($\Delta L^*$) |
| --- | --- |
| Example 1 | 1.76 ± 0.21 |
| Hydroquinone (positive control group) | 1.90 ± 0.13 |
| Vehicle (negative control group) | 0.50 ± 0.16 |

As shown in Table 9 above, the ginseng berry extract of Example 1 of the present invention showed skin-color brightness similar to that of hydroquinone. This is because the ginseng berry extract improves pigmentation, resulting from UV light, to make the skin color bright.

Experimental Example 4

Effects of Moisturizing Skin and Relieving Atopic Symptoms

1) Induction of Differentiation of Human Keratinocytes

The effect of the ginseng berry extract of Example 1 of the present invention on the promotion of cell differentiation was examined by measuring the amount of CE (cornified envelop) produced during keratinocytes and the human keratinocyte cell line (HaCaT).

Primarily cultured human keratinocytes were placed in a culture flask and allowed to adhere to the bottom of the flask, and then the test materials shown in Table 10 below were added to the culture media at varying concentrations. The cells were cultured for 5 days to a confluency of about 70-80%. The cultured cells were harvested and washed with PBS (phosphate buffered saline), and then 1 ml of 10 mM Tris-HCl buffer (pH 7.4), containing 2% SDS (sodium dodecyl sulfate) and 20 mM DTT (dithiothreitol), was added to the cells. The cell solution was sonicated, boiled and centrifuged, and the resulting precipitate was suspended in 1 ml of PBS and measured for absorbance at 340 nm. Meanwhile, a portion of the solution after the sonication was taken and measured for its protein content, and the measured value was used as a standard for evaluating the degree of cell differentiation. A low calcium (0.03 mM)-treated group and a high calcium (1.2 mM)-treated group were used as a negative control groups and a positive control group, respectively. The test results are shown in Table 10 below.

TABLE 10

| Test materials | | Differentiation (%) of keratinocytes |
|---|---|---|
| Control group | Low calcium-treated group (0.03 mM $Ca^{2+}$) | 100 |
| | High calcium-treated group (1.2 mM $Ca^{2+}$) | 210 |
| | Red ginseng extract (100 ppm) | 104 |
| Example 1 | 1 ppm | 115 |
| | 10 ppm | 120 |
| | 100 ppm | 124 |

From the results of Table 10, it could be seen that the ginseng berry extract of Example 1 of the present invention stimulated the differentiation of keratinocytes.

2) Effect of Expressing Transglutaminase in Human Skin Cell Line

Human skin cells were placed in a 96-well plate at a concentration of $5 \times 10^4$ cells/well and attached to the plate for 24 hours. The attached skin cells were treated with the test material, and after 2 days, the medium was removed, and the cells were stored in a refrigerator at 20° C. The cells were frozen and thawed twice, disrupted and treated with acetone:ethanol (1:1, v/v), stored at −20° C. The treated cells were left to stand at 4° C. for 30 minutes to immobilize the cells. Then, the cells were left to stand at room temperature to evaporate the organic solvent and were blocked with 1% bovine serum albumin. The blocked cells were allowed to react with a transglutaminase antibody (primary antibody), an HRP anti-mouse antibody (secondary antibody), and the color development of the cells was carried out by the addition of OPD (o-phennyldiamine). The expression level of transglutaminase in the cells was measured by measuring the absorbance at 490 nm, and the correction was carried out by measuring the background at 630 nm. A low calcium (0.03 mM)-treated group and a high calcium (1.2 mM)-treated group were used as a negative control group and a positive control group, respectively, and the test results are shown in Table 11 below.

TABLE 11

| Test materials | | Transglutaminase expression (%) |
|---|---|---|
| Control group | Low calcium-treated group (0.03 mM $Ca^{2+}$) | 100 |
| | High calcium-treated group (1.2 mM $Ca^{2+}$) | 140 |
| | Red ginseng extract | 131 |
| Example 1 | 1 ppm | 135 |
| | 10 ppm | 175 |
| | 100 ppm | 210 |

From the results of Table 11, it could be seen that the ginseng berry extract of Example 1 of the present invention showed an about 2-fold increase in the expression of transglutaminase compared to the control group. This suggests that the ginseng berry extract of Example 1 of the present invention increases the expression of transglutaminase.

3) Effect of Increasing Epidermal Lipid (Total Ceramide) in Human Skin

In order to evaluate the effect of the ginseng berry extract of Example 1 on an increase in lipid synthesis in human skin, 0.5 wt % of Carbopol ETD 2020, 0.45% of TEA, 5 wt % of the test material and the balance of deionized water were used. On 12 adult men and women, a region corresponding to the diameter of a polypropylene conical tube was marked on the arm, and then was applied with 20 μl of each of control groups and the ginseng berry extract of Example 1 twice every day. The subjects were divided into two groups, and the production of lipid in the applied region was analyzed in the following manner by extracting lipid at day 3 and day 11. Specifically, the arm was washed with service water, and then subjected to tape stripping once with Scotch 810 Magic tape. Then, 1 ml of a mixture of cyclohexane/ethanol (4:1) was added to the tape using a cut 50-ml polypropylene conical tube as a reservoir and stirred for about 1 minute, and then the solution was transferred into a fresh tube. Then, the tape was treated with 1 ml of a mixture of cyclohexane/ethanol (1:1) in the same manner as described above, and the solution was collected in the tube. Then, the solution was dried with nitrogen gas at 50° C. and dissolved in 500 μl of chloroform/methanol (2:1). Then, each of the test materials was added dropwise to a silica gel TLC (thin layer chromatography) plate using Automated TLC sampler-4 (CAMAG Inc.) and was developed with developing solvents, having the composition ratios shown in Table 12, using AMD (automated multiple development).

TABLE 12

| | Chloroform | Methanol | Water | Acetic acid | Hexane | Diethyl ether | Petroleum ether | Solvent migration distance (cm) |
|---|---|---|---|---|---|---|---|---|
| First | 40 | 10 | 1 | | | | | 3.0 |
| Second | 190 | 9 | | 1 | | | | 6.5 |
| Third | | | | 2 | 12 | 3 | | 7.5 |
| Fourth | | | | | | | 100 | Top |

After the TLC plate was developed, the size of each band was measured at a wavelength of 570 nm using TLC scanner-II (CAMAG; densitometer). The production of ceramide in each treated group, expressed relative to 100% for the non-treated group, is shown in Table 13 below.

TABLE 13

| Test materials | | After 3 days of treatment (%) | After 11 days of treatment (%) |
|---|---|---|---|
| Control groups | Untreated | 100 | 100 |
| | Vehicle | 103 | 98 |
| | Glycerin (5%) | 102 | 94 |
| Example 1 (5%) | | 108 | 116 |

As shown in Table 13 above, after 3 days of treatment, the group treated with the ginseng berry extract of Example 1 showed an increase in lipid production of about 5-8% compared to the negative control groups (untreated/vehicle) and showed an increase of about 6% compared to the positive control group (glycerin). After 11 days of treatment, the group treated with the ginseng berry extract of Example 1 showed an increase in lipid production of about 16% compared to the negative control group and showed an increase of about 22% compared to the positive control group. This suggests that the ginseng berry extract of Example 1 of the present invention increases the production of ceramide.

4) Increase in Skin Moisturizing Ability in Human Body

Fifty 50-60-years old men and women having xerosis cutis were divided into two groups, and the faces of the subjects in each of the groups were applied with Example 2 and Comparative Example twice every day for 4 weeks. Before the initiation of application, at 1 week, 2 weeks and 4 weeks after the initiation of application and at 2 weeks after the end of application (a total of 6 weeks), the moisture content of the skin of the subjects was measured with a koniometer in constant temperature and constant humidity conditions (24° C. and 40% relative humidity), and the measurement results are shown in Table 14. The test results were expressed as the percentages of increases in values, measured after application, relative to koniometer values, measured immediately before the initiation of application.

TABLE 14

| | Increase (%) in water content | | | |
|---|---|---|---|---|
| Test materials | After 1 week | After 2 week | After 4 week | After 6 week |
| Example 2 | 34 | 41 | 42 | 33 |
| Comparative Example 2 | 30 | 34 | 34 | 15 |

The Koniometer is a device of measuring the moisture content of the skin by measuring the electrical conductivity of the epidermis. As shown in Table 14, the group applied with Example 2 containing the ginseng berry extract of Example 1 showed an increase in the skin moisture content compared to the control group applied with Comparative Example 2. Also, the skin moisture value, measured at 2 weeks after the application of the nourishing cream of Example 2 was terminated (after a total of 6 weeks), was similar to the skin moisture values, measured at 1-2 weeks after the initiation of application of the nourishing cream. This suggests that the application of the inventive ginseng berry extract can maintain the skin moisture content for a given period of time, even when the cream of Example 2 is not applied for that period.

5) Effect of Relieving Atopic Dermatitis

The effect of relieving atopic symptoms was measured in the following manner. Fifty 10-50-year old persons, diagnosed as atopic symptoms (itching, erosion or severe xerosis) or showing symptoms similar to atopy in visual observation, were divided into 2 groups. The two groups were provided with Example 2 and Comparative Example 2, respectively, and the creams of Example 2 and Comparative Example 2 were applied on the subject's portions, showing atopic symptoms, twice every day for 12 weeks. To evaluate the effect of the test material, the degree of relief was evaluated subjectively by the person in question through survey after 12 weeks of treatment. In the survey, atopic dermatitis symptoms were divided into "itching", "xerosis", "keratinozation", "scale", "erythema", "swelling", "skin cracking" and "oozing and eczema", and if the subjects had said symptoms, the degree of relief for each symptom was evaluated. The evaluated scores were averaged and the effect of relieving atopic symptoms was individually evaluated. The evaluation results are shown in Table 15 below.

TABLE 15

| | Numbers of respondents | | | |
|---|---|---|---|---|
| Tested materials | Significantly relieved | Relieved | Not changed | Worsen |
| Example 2 | 2 | 4 | 14 | 0 |
| Comparative Example 2 | 6 | 8 | 6 | 0 |

As shown in Table 15 above, atopic symptoms in the group applied with the formulation containing the ginseng berry extract of Example 1 were generally relieved compared to those in the control group.

Experimental Example 5

Relief of Acne and Skin Troubles

1) Sebum Regulating Effect: Inhibitory Effect Against 5-Alpha-Reductase Activity Adult SD (Sprague-Dawley) male rats (7-8-week old) were sacrificed with diethyl ether, the abdominal prostate was extracted, and the connective tissue was removed. The prostate tissue was finely cut in buffer (0.32 M sucrose, 0.1 mM dithiothreitol and 20 mM sodium acetate), and was then suspended with a stirrer. The suspension was centrifuged, and the supernatant was collected. 5-alpha-reductase was partially purified from the supernatant in order to the activity thereof.

A portion of the above-collected supernatant was taken and placed in buffer containing 0.2 M monobasic acid and 0.2 M dibasic acid. Then, the solution was allowed to react with a $^3$H-bound substrate (testosterone), and the production of the product dihydrotestosterone was measured.

The reaction solution contained 1 mM dithiothreitol, 40 mM sodium phosphate (pH 6.5), 50 μM NADPH, [1,2,6,7-$^3$H] testosterone/testosterone ($2.2 \times 10^9$ mole), 0.8 mg enzyme suspension and 565 μl protein.

The ginseng berry extract of Example 1 was dissolved in 10% ethanol and added in an amount of 100 μg extract/10 μl 10% ethanol per reaction. As a control group, the same volume of the solvent was used, and as the positive control group, riboflavin was used.

The reaction was initiated at the same time as adding the enzyme suspension and was carried out at 37° C. for 30 minutes, and then the reaction material was extracted with 1 μl of ethyl acetate. 100 μl of the ethyl acetate phase was developed on silica plastic sheet kieselgel 60 F254 using acetate-cyclohexane (1:1) as a developing solvent system.

The plastic sheet was dried in air, and then a VAS system was used to measure of isotopes. Specifically, the dried plastic sheet together with an X-ray film was placed in a VAS cassette, and after 1 week, the amounts of the testosterone and dihydrotestosterone isotopes remaining on the film were measured. The measurement results are shown in Table 16 below.

TABLE 16

| Test materials | T (dpm) | DHT (dpm) | Conversion (%) | Inhibition (%) |
|---|---|---|---|---|
| Example 1 | 6878 | 2355 | 25.5 | 39.9 |
| Control group | 7520 | 5536 | 42.4 | — |
| Positive control group | 6300 | 2530 | 28.7 | 32.4 |

(1) T: 3H radioactivity shown in the testosterone region;
(2) DHT: 3H radioactivity shown in the dihydrotestosterone region;
(3) conversion: radioactivity in the DHT region/total radioactivity; and
(4) inhibition: 100 × (conversion of control group-conversion of sample)/conversion of control group From the results of Table 16 above, it can be seen that the ginseng berry extract had the effect of inhibiting 5-alpha-reductase.

2) Lipogenesis Inhibitory Effect

The degree of lipogenesis in sebaceous glands was evaluated by evaluating the inhibition of lipogenesis through the quantification of carbon uptake required for lipogenesis.

Specifically, the ear tissue of hamsters, having abundant sebaceous glands, was biopsied, and the degree of lipogenesis was evaluated by comparatively quantifying the control group and the test materials using a radioactivity meter in C14-labeled media for 6 hours. In the test material groups, the right ear tissue of hamsters was used and 0.01% test material solutions were added to the media, and in the control group, the left ear tissue of hamsters was used and 0.01% saline was added to the media. The test results are shown in Table 17 below.

Meanwhile, the inhibition (%) in Table 17 was calculated according to the following equation 4 and was expressed as the average of 4 hamsters.

Inhibition(%)=test group/control group×100    [Equation 4]

TABLE 17

| Test material | Inhibition (%) |
|---|---|
| Example 1 | 47 |
| Positive control group (retinoic acid) | 52 |

From the results of Table 17 above, it can be seen that the ginseng berry extract of Example 1 according to the present invention has the effect of inhibiting lipogenesis.

3) Effect of Reducing Comedos

To confirm the effect of reducing comedos, the ginseng berry extract of Example 1 used in the present invention was dissolved in 1,3-butyleneglycol to form a 1% solution, which was then used as a test material in clinical experiments employing rabbits.

0.2 ml of 50% oleic acid/paraffin oil as a comedo inducer was applied to the ear of white rabbits in the morning and rubbed with a cotton swab. The application was carried out twice a day for 1 month. Specifically, in the morning, 50% oleic acid/paraffin was applied, and in the afternoon, the test material was applied. Comodes were developed from about 10 days after the application of the comedo inducer, and the application of the ginseng berry extract of Example 1 in the afternoon led to gradual decreases in the number and size of comedos from 2 weeks after the application.

The ear tissue was biopsied, and horny substance was removed therefrom. Then, the size of comedos in the tissue was observed under a microscope, and the observation results are shown in Table 18 below.

TABLE 18

| Test materials | Average of measured comedo sizes (0.1 mm) N = 3 |
|---|---|
| Control group (untreated) | 1.78 |
| Oleic acid (OA) | 3.5 |
| Oleic acid (OA) + Example 1 | 2.3 |

From the results of Table 18, it could be seen that, in the rabbits treated with the ginseng berry extract of Example 1 of the present invention, the comedos were significantly reduced. That is, due to the ginseng berry extract of Example 1, a decrease in sebum was shown and, as a result, skin hyperkeratinization was reduced, leading to a reduction in comedos.

4) Effect of Inhibiting Sebum Secretion

To measure the effect of relieving oily skin, Example 2 (containing ginseng berry extract) was applied to the forehead of twenty 20-45-year old women twice (morning and afternoon) a day, and Comparative Example 2 was applied to the forehead of other ten 20-45-year old women in the same manner. At 1 week, 2 week, 3 week and 4 week after the application, the sebum secretion of the skin was measured with a Sebumeter SM810. The experiment was carried out at a temperature of 20° C. and a relative humidity of 20%, and the measurement results are shown in Table 19. The results are expressed as the average of ten subjects. In Table 19, a value of more than 220 indicates oily skin, and a value of 100-220 indicates normal skin.

TABLE 19

| | Sebum secretion inhibitory effect | | | | |
|---|---|---|---|---|---|
| Test materials | Before application | After 1 week | After 2 weeks | After 3 weeks | After 4 weeks |
| Comparative Example 2 | 245 | 240 | 239 | 235 | 230 |
| Example 2 | 245 | 236 | 231 | 218 | 209 |

From the results of Table 19, it could be seen that the nourishing cream containing the ginseng berry extract of Example 1 of the present invention showed the effect of inhibiting the excessive secretion of sebum, suggesting that it had a sebum regulating effect.

5) Anti-Inflammatory Effect: Effect of Producing Prostaglandin E2 (Pge2) Production In order to examine the prostaglandin E2 (PGE2) production inhibitory effect of the ginseng berry extract according to the present invention, the following test was carried out (reference: Jeffrey, K. H., Anglea, S. W., Zoe, S., and Rhia C. M. Intracellular Measurement of Prostaglandin E2: Effect of Anti-inflammatory Drugs on Cyclooxygenase Activity and Prostanoid Expression, Analytical Biochemistry, 1999, 271, 18-28).

First, fibroblasts isolated from human epidermal tissue were cultured in a $CO_2$ incubator for 24 hours, and the medium was replaced with a medium containing FBS (fetal bovine serum). Then, the cells were cultured for 2 hours, and then treated with each of mixtures of the ginseng berry extract of Example 1 with distilled water, having 1 μg/mL, 10 μg/mL and 100 μg/mL. Then, the cells were cultured in a $CO_2$ incubator in conditions of 37° C. and 5% (v/v) for 2 hours.

Then, the cells were treated with 50 μm of a mixture of calcium ionophore A23187 with arachidonic acid as a prostaglandin E2 stimulus for 5 minutes. Then, the cells were lysed and measured for absorbance at 450 nm using an ELISA reader to quantify prostaglandin E2, and the analysis results are shown in Table 20. In Table 20, the inhibition (%) was calculated based on the difference in prostaglandin E2 production between the skin fibroblasts, not treated with the ginseng berry extract of Example 1, and the skin fibroblasts treated with the ginseng berry extract of Example 1, and was expressed as the average of five measurements.

TABLE 20

| Test materials | Concentration (μg/mL) | Prostaglandin E2 (pg/$10^5$ cells) | Inhibition (%) |
|---|---|---|---|
| Negative control group | — | 25.2 4.4 | — |
| Arachidonic acid | — | 385.1 ± 9.1 | — |
| Arachidonic acid + | 1 | 289.6 ± 6.5 | 24.8 |
| Example 1 | 10 | 246.4 ± 8.6 | 36.0 |
|  | 100 | 195.6 ± 14.3 | 49.2 |

From the results of Table 20, it could be seen that the ginseng berry extract of Example 1 according to the present invention could inhibit prostaglandin E2 production caused by the stimulus.

6) Anti-Inflammatory Effect: Effect of Inhibiting Cyclooxygenase-2 (Cox-2) Biosynthesis Induced by LPS (Lipopolysaccharide)

Human fibroblasts were cultured in a 12-well plate at a concentration of $10^5$ cells/well, and then treated with LPS. Then, the medium was replaced with each of media containing 1 ppm, 10 ppm and 100 ppm of the ginseng berry extract of Example 1. At 2 days of culture, the cells were harvested, and the production of cyclooxygenase-2 (COX-2) in the cells was quantified with a densitometer using a Western blot method. The measurement results were expressed relative to 100 for a control group and are shown in Table 21 below. Herein, the control group was an untreated group cultured without being treated with the ginseng berry extract of Example 1.

TABLE 21

| Test materials (ppm) | COX-2 biosynthesis (%) |
|---|---|
| Example 1    100 | 15 |
|              10 | 35 |
|              1 | 71 |
| Control group | 100 |

As can be seen from the results of Table 21, the ginseng berry extract of Example 1 according to the present invention showed the effect of concentration-dependently reducing the biosynthesis of cyclooxygenase-2, induced by inflammatory LPS, to inhibit an inflammatory reaction, thus relieving skin troubles.

7) Anti-Inflammatory Effect: Effect of Inhibiting Tumor Necrosis Factor-α Biosynthesis Induced by LPS (Lipopolysaccharide)

Human keratinocytes were cultured in a 12-well plate at a concentration of $10^5$ cells/well and treated with LPS, and then the medium was replaced with each of 1 ppm, 10 ppm and 100 ppm of the ginseng berry extract of Example 1. After 6-24 hours of culture, the cells were harvested, and the production of tumor necrosis factor-α in the cells was quantified using an ELISA (Pharmingen 555212) method. The measurement results were expressed relative to 100 for a control group and are shown in Table 22. Herein, the control group was an untreated group cultured without being treated with the ginseng berry extract of Example 1.

TABLE 22

| Test materials (ppm) | THF-α biosynthesis (%) |
|---|---|
| Example 1    100 | 14 |
|              10 | 41 |
|              1 | 69 |
| Control group | 100 |

As can be seen from the results of Table 22, the ginseng berry extract of Example 1 according to the present invention can concentration-dependently reduce tumor necrosis factor (TNF-α) biosynthesis, induced by inflammatory LPS, to inhibit an inflammatory reaction, which can occur due to necrosis factor (TNF-α) biosynthesis, thus relieving skin troubles.

8) Effect of Inhibiting LPS-Induced NO (Nitrogen Oxide) in Macrophages

To examine the anti-inflammatory effect of the ginseng berry extract of the present invention, a test of the inhibition of LPS-induced NO (nitrogen oxide) on macrophages was carried out.

Macrophages (raw 264.7 cells) were cultured in 10% serum-containing medium in a condition of 5% $CO_2$. The cells were cultured in a 96-well plate to a concentration of $2 \times 10^5$ cells, treated with LPS (1 μg/ml) and then treated with each of the ginseng berry extract of Example 1 and red ginseng extract. The treated cells were stored at 37° C. for 1 hours, and the production of NO in the cells was measured to compare the effects of inhibiting LPS-induced NO. The measurement of NO production was carried out using a Griess reaction method (Minghetti, L. et al., 1991, Glia 19. 152-160), and the measurement results are shown in FIG. 5.

Figure 5:
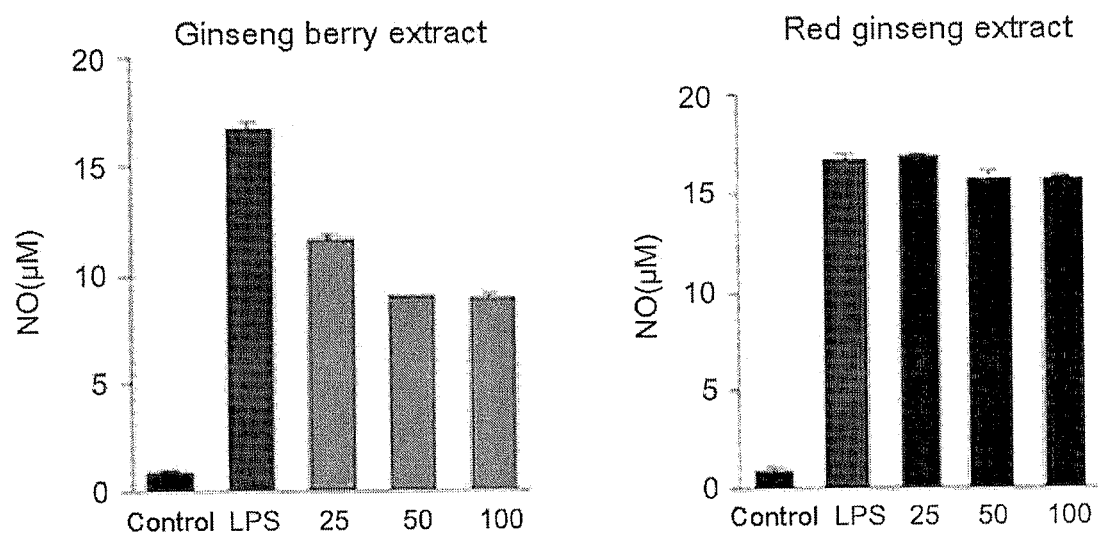
FIG. 5 is a graphic diagram showing the comparison of nitrogen monoxide inhibitory effect between the ginseng berry extract of Example 1 and a red ginseng extract.

As can be seen from the results of FIG. 5, the ginseng berry extract of Example 1 according to the present invention effectively inhibited the production of NO as an inflammatory factor (cytokine), and the effect thereof was significantly excellent compared to the effect of the red ginseng extract. Accordingly, it is expected that the ginseng berry extract of Example 1 according to the present invention will heal wounds, caused by skin troubles, through the regulation of inflammatory reactions, and inhibit wrinkle formation.

9) Effect of Relieving Acne and Skin Troubles

The face of ten women, having skin troubles including acne, were washed with soap in a constant-temperature and constant-humidity room and adapted for 30 minutes. The numbers of acne lesions and inflammatory acne lesions were counted in order to measure the degree of skin troubles.

The test subjects were applied with each of the nourishing creams of Example 2 and Comparative Example 2, and then the degree of acne and skin troubles was compared between Example 2 and Comparative Example 2. The test results are shown in Table 23 below.

TABLE 23

|  | Example 1 (5 persons) | Comparative Example 1 (5 persons) |
|---|---|---|
| Skin trouble relief | 80% | 20% |

As can be shown from the results of Table 23, when Example 2 containing the ginseng berry extract of Example 1 of the present invention was applied for 4 weeks, the number of acne lesions was reduced, and inflammatory troubles were relieved.

Experimental Example 6

Effect of Improving Skin Complexion

1) NO Productivity of Ginseng Berry Extract in HUVEC (Human Umbilical Vein Endothelial Cells)

Human vascular endothelial cells contain eNOS (endothelial nitric oxide synthase), which produces NO (nitric oxide) to enlarge blood vessels and promote blood circulation. Human vascular endothelial cells were cultured, and the culture medium was treated with each of ginseng berry extract (FIG. 6) and general red ginseng extract (FIG. 7). The production of NO in the cells was compared between the extracts. Specifically, vascular endothelial cells were attached to a gelatin-coated 24-well plate at a concentration of $2.5 \times 10^4$ cells/well, and then cultured in growth medium for 24 hours. The vascular endothelial cells were pretreated with each of the ginseng berry extract of Example 1 of the present invention, the red ginseng extract and a control group for 12 hours. The endothelial cells were treated with 10 µmol/L DAF-FM diacetate (Molecular Probe, OR) in FBS-free M199 medium at 37° C. for 30 minutes. The vascular endothelial cells were washed three times with FBS-free M199 medium, and then the cells were placed in a parallel plate flow chamber and excited with light emitted from a mercury lamp. The excitation wavelength was 488 nm, and NO-bound DAF indicates fluorescence at 515 nm. The cells were photographed with a confocal laser microscope (Atto Bioscience, USA), and fluorescence intensity was analyzed with Image-ProPlus v4.5 software (Media Cybernetics, San Diego, Calif., USA). Based on the measured fluorescence intensity, the production of NO in the test group was compared with the control group. The test results are shown in FIGS. 6 and 7.

Figure 6:
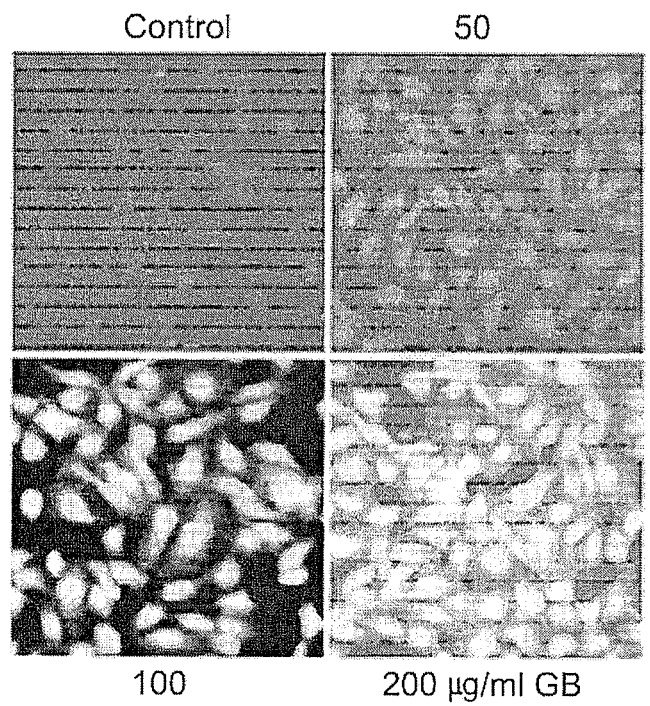
FIG. 6 is a graphic diagram showing the production of NO by the ginseng berry extract of Example 1.
Figure 6:
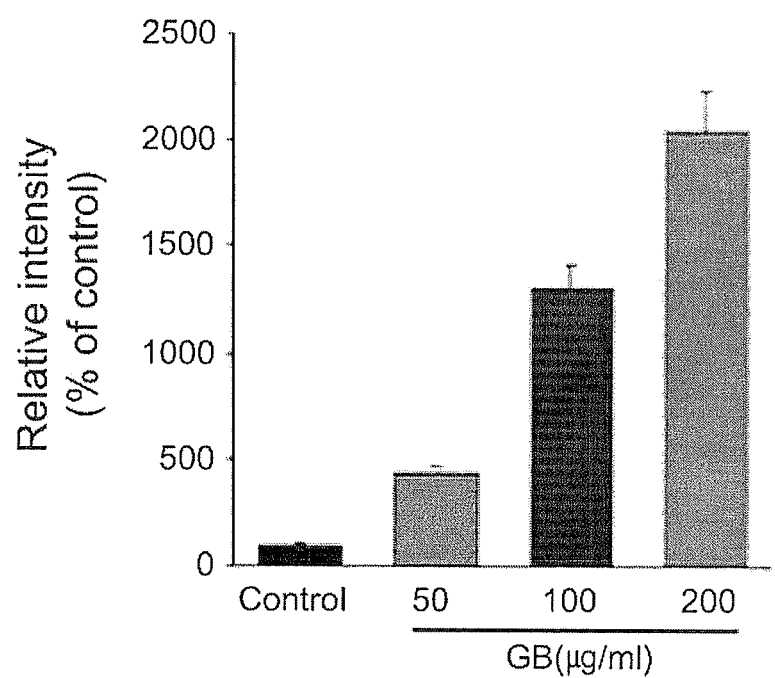
Figure 7:
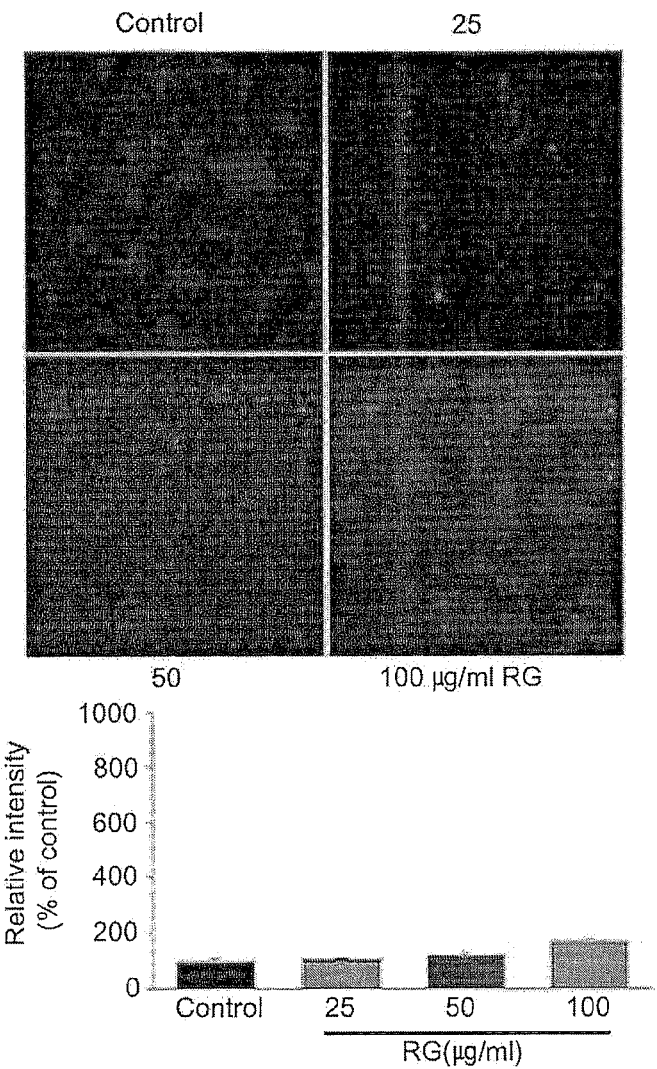
FIG. 7 is a graphic diagram showing the production of NO by a red ginseng extract.

As can be seen from the results of FIGS. 6 and 7, the ginseng berry extract of Example 1 according to the present invention showed a NO production of 500-1300% compared to that of the control group, and the general red ginseng extract showed a NO production of 100-200% compared to that of the control group (at the same concentration of 50-100 µg/ml). Accordingly, the ginseng berry extract of Example 1 according to the present invention showed significantly excellent NO productivity in vascular endothelial cells compared to the red ginseng extract. Due to this excellent NO (nitric oxide) productivity of the ginseng berry extract of Example 1, the ginseng berry extract enlarges capillary blood vessels and promotes blood circulation, and thus it can ensure the smooth supply of nutrients to the skin, inhibit skin aging and improve skin complexion.

2) Effect of Improving Human Skin (Face) Complexion

To evaluate the effect of the ginseng berry extract of the present invention on the promotion of blood circulation in the skin, blood circulation in the skin was measured using LDPI (laser doppler perfusion imager). LDPI is widely known as a device of measuring blood circulation in the skin and is a very sensitive device capable of measuring not only the rate and amount of blood flow in the capillary blood vessels of the skin, but also blood flow in small arteries and small veins.

The face of test subjects was washed with soap in a constant-temperature and constant-humidity room and adapted for 30 minutes. Initial values were measured using LDPI and an IR (Infrad) camera as a skin temperature measuring device. The test subjects consisted of 20 women, having cold hand and foot, the initial blood flow of the lower forehead portion was measured with LDPI, and initial skin temperatures of the forehead, the under-eye portion and the cheek were measured using the IR camera.

After Example 2 was applied to the test subjects for 1 week, the blood flow and skin temperature of the subjects were compared with the initial measurement values. The measurement results are shown in Tables 24 and 25 below.

TABLE 24

LDPI results before and after application

| Face | Before application | After 1 week of application |
|---|---|---|
| Average value | 0.952 | 1.169 |

TABLE 25

IR results before and after application

| | Forehead | Under-eye | Cheek |
|---|---|---|---|
| Before application | 32.26 | 32.02 | 30.44 |
| After 1 week of application | 33.87 | 33.69 | 33.57 |

As can be seen from the results of Tables 24 and 25, when Example 2 containing the ginseng berry extract of the present invention was applied, the complexion of the face of the subjects was improved due to the improvement of peripheral blood circulation. This suggests that, when the ginseng berry extract of the present invention is applied, it can effectively supply nutrients to the skin and can inhibit delay skin aging.

Reference Example 1

Isolation of Epididymal Adipose Tissue

The epididymal adipose tissue of Sprague-Dawley (hereinafter referred to as "SD") male white rats was isolated, and then finely cut with scissors, and 0.1% collagenase in DMEM without phenol red was added thereto. Then, the tissue was cultured at 37° C. for 2 hours and filtered, thus obtaining adipocytes.

Experimental Example 7

Effect of Promoting Neutral Fat Degradation in Male SD Rats

To evaluate the effect of promoting the degradation of neutral fat in the adipocytes of male SD white rats, an experiment was carried out using the adipocytes isolated according to the method of Reference Example 1.

Fatty acid-free DMEM (Dulbeco's modified eagles medium) containing 0.5% BAS (bovine serum albumin, BAS) was added to adipocytes for use in the experiment. The quantification of glycerol was performed using a GPO-trinder kit (Sigma, St. Louis, Mo., USA) according to a color development method, and the absorbance at 540 nm was measured using an ELISA reader.

As a control group, a medium, not containing the test material or the comparative material, was used. Each of the ginseng berry extract of Example 1 and the red ginseng extract was added to the medium at each of concentrations of 10 ppm, 100 ppm and 200 ppm. Because fat is degraded into fatty acid and glycerol when it is hydrolyzed, the degree of lipolysis was determined by measuring the concentration of glycerol released from the adipocytes into the medium. The measurement results were expressed relative to 100 for the control group and are shown in FIG. 8.

Figure 8:
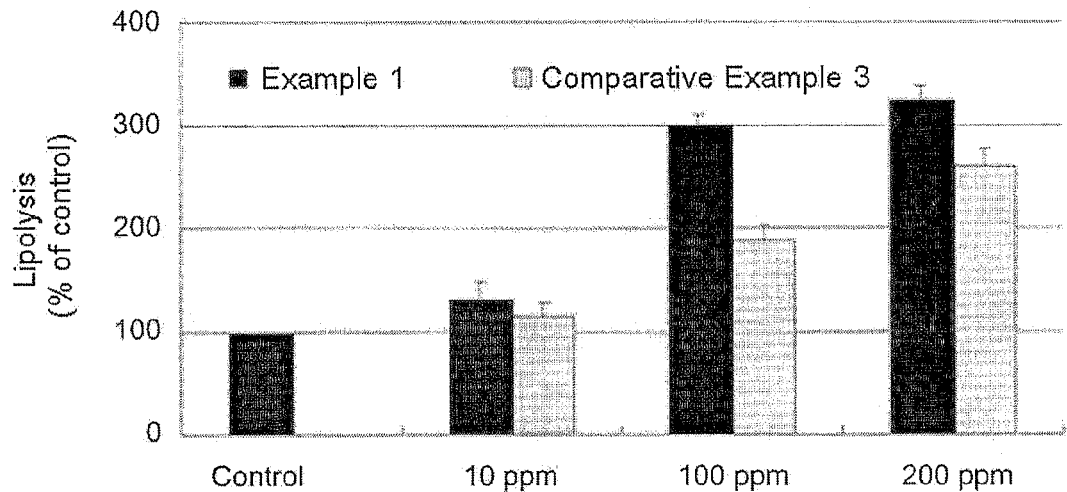
FIG. 8 is a graphic diagram showing the lipolytic effects of the ginseng berry extract of Example 1 and the red ginseng extract of Comparative Example 2.

As can be seen in FIG. 8, when the cells were treated with varying concentrations of the ginseng berry extract, the group treated with 10 ppm of the ginseng berry extract showed a lipolytic effect about 1.3 times higher than that of the control group. Also, the group treated with 100 ppm of the ginseng berry extract showed a lipolytic effect about 3 times higher than that of the control group, and the group treated with 200 ppm of the ginseng berry extract showed a lipolytic effect about 3.3 times higher than that of the control group. In addition, the group treated with the ginseng berry extract showed a lipolytic effect higher than that of the group treated with the red ginseng extract.

Experimental Example 8

Effect on Lipid Metabolism in Animals

In order to examine the effect of the inventive composition on lipid metabolism in obesity animals by high-fat diet, male SD white rats were selected as models and used in experiments.

In order to examine how the ginseng berry extract has an effect on obesity induced by high-fat diet, 6-week-old rats were adapted for 1 week and randomly grouped into several test groups, each consisting of 10 animals. Specifically, as shown in Table 26 below, the animals were divided into a normal fat diet group, a high-fat diet group, a high-fat diet+ 0.5% ginseng berry extract group, a high-fat diet+1% ginseng berry extract group and a high-fat diet+1.5% ginseng berry extract group. In addition, animals to be fed with red ginseng extract as control were grouped in this manner.

TABLE 26

| | |
|---|---|
| 1 | Normal diet (C) |
| 2 | High-fat diet (HF) |
| 3 | High-fat diet (HF) + 0.5% *ginseng* berry extract (GB) |
| 4 | High-fat diet (HF) + 0.5% red *ginseng* extract (RG) |
| 5 | High-fat diet (HF) + 1.0% *ginseng* berry extract (GB) |
| 6 | High-fat diet (HF) + 1.0% red *ginseng* extract (RG) |
| 7 | High-fat diet (HF) + 1.5% *ginseng* berry extract (GB) |
| 8 | High-fat diet (HF) + 1.5% red *ginseng* extract (RG) |

The experimental diets were fed for 8 weeks and were prepared according to the compositions shown in Table 27 below. Herein, the experimental diets were prepared based on AIN-93G purified diet such that fat accounted for 36% of total calorie (18% based on diets), and the normal fat diet was prepared such that it accounted for 17% of total calorie (7% based on diet).

TABLE 27

Feed composition ratio of each test group

| Test groups | 1[1)] | 2 | 3 and 4 | 5 and 6 | 7 and 8 |
|---|---|---|---|---|---|
| Corn starch | 529.486 | 419.486 | 414.486 | 409.486 | 404.483 |
| Casein | 200.0 | 200.0 | 200.0 | 200.0 | 200.0 |
| Sucrose | 100.0 | 100.0 | 100.0 | 100.0 | 100.0 |
| Bean oil | 70.0 | 180.0 | 180.0 | 180.0 | 180.0 |
| Ginseng berry extract or red ginseng extract | — | — | 5 | 10 | 15 |
| Fiber | 50.0 | 50.0 | 50.0 | 50.0 | 50.0 |
| Mineral mixture[2)] | 35.0 | 35.0 | 35.0 | 35.0 | 35.0 |
| Mineral mixture[3)] | 10.0 | 10.0 | 10.0 | 10.0 | 10.0 |
| L-cysteine | 3.0 | 3.0 | 3.0 | 3.0 | 3.0 |
| Choline bitartrate | 2.5 | 2.5 | 2.5 | 2.5 | 2.5 |
| Tert-butyl hydroquinone | 0.014 | 0.014 | 0.014 | 0.014 | 0.014 |
| Total energy (Kcal) | 3498 | 4502 | 4500 | 4496 | 4490 |

[1)]normal diet: AIN-93G diet;
[2)]mineral mixture: AIN-93G mineral mixture (g/kg mix);
[3)]vitamin mixture: AIN-93G vitamin mixture (g/kg mix)

During the feeding period of the experimental diets, the diet intake and the weight were measured three times a week, and after completion of the feeding of the experimental diets, the weight was finally measured. The measurement results are shown in Table 28 and FIG. 9.

TABLE 28

Difference in weight between groups and feed intake

| Test groups | Diet intake | Weight (g) before experiment (g) | Feed intake (g/day) |
|---|---|---|---|
| 1 | Normal diet (C) | 178.6 ± 10.1 | 27.2 ± 3.5 |
| 2 | High-fat diet (HF) | 176.9 ± 14.2 | 26.5 ± 5.4 |
| 3 | High-fat diet (HF) + 0.5% *ginseng* berry extract (GB) | 174.5 ± 17.2 | 28.3 ± 8.4 |
| 4 | High fat diet (HF) + 0.5% red *ginseng* extract (RG) | 172.2 ± 16.2 | 27.4 ± 7.4 |
| 5 | High fat diet (HF) + 1.0% *ginseng* berry extract (GB) | 176.1 ± 20.8 | 26.4 ± 3.2 |
| 6 | High-fat diet (HF) + 1.0% red *ginseng* extract (RG) | 178.6 ± 17.6 | 26.8 ± 5.1 |

TABLE 28-continued

Difference in weight between groups and feed intake

| Test groups | Diet intake | Weight (g) before experiment (g) | Feed intake (g/day) |
|---|---|---|---|
| 7 | High-fat diet (HF) + 1.5% *ginseng* berry extract (GB) 1.5% | 177.2 ± 19.1 | 26.8 ± 6.1 |
| 8 | High-fat diet (HF) + 1.5% red *ginseng* extract (RG) | 175.8 ± 18.4 | 27.1 ± 4.2 |

Figure 9:
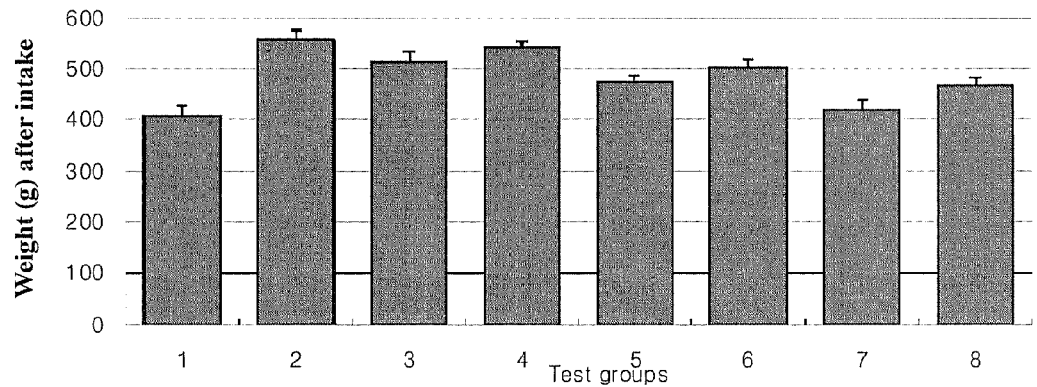
FIG. 9 is a graphic diagram showing the change in weight during the 8-week intake of the ginseng berry extract or the red ginseng extract together with a high-fat diet.

As shown in Table 28 above, before the start of the experiment, there was no difference in weight between the test groups and, in addition, there was no significant difference in diet intake between the groups. However, as shown in FIG. 9, the weight after diet intake was 408.2±20.1 for the normal diet group, and was 557.2±17.5 for the high-fat diet group (control group), which was increased compared to that of the normal diet group. Also, the weights of the groups fed with 0.5%, 1.0% and 1.5% ginseng berry extract, respectively, were 512.3±20.4, 475.2±10.7 and 420.9±16.8, respectively, suggesting that the increase in weight in the ginseng berry extract diet groups was significantly inhibited in a manner dependent on the concentration of the ginseng berry extract ($P<0.05$). Also, the weights of the groups fed with 0.5%, 1.0% and 1.5% red ginseng extract, respectively, were 539.7±15.2, 502.1±16.8 and 465.1±17.2, respectively, which were lower than that of the high-fat diet group, but higher than those of the ginseng berry extract diet groups. This suggests that the ginseng berry extract is more effective in inhibiting the increase in weight than the red ginseng extract and that the ginseng berry extract can assist in the prevention and reduction of obesity.

Experimental Example 9

Measurement of Epididymal Adipose Tissue Weight

After the test groups 1-8 in Experimental Example 8 were fed with the diets, the animals were sacrificed and the epididymal adipose tissue of the animals was isolated. The isolated epididymal adipose tissue was washed with physiological saline and filtered through filter paper to remove water. Then, the weight of the epididymal adipose tissue was measured, and the measurement results are shown in FIG. 10.

Figure 10:
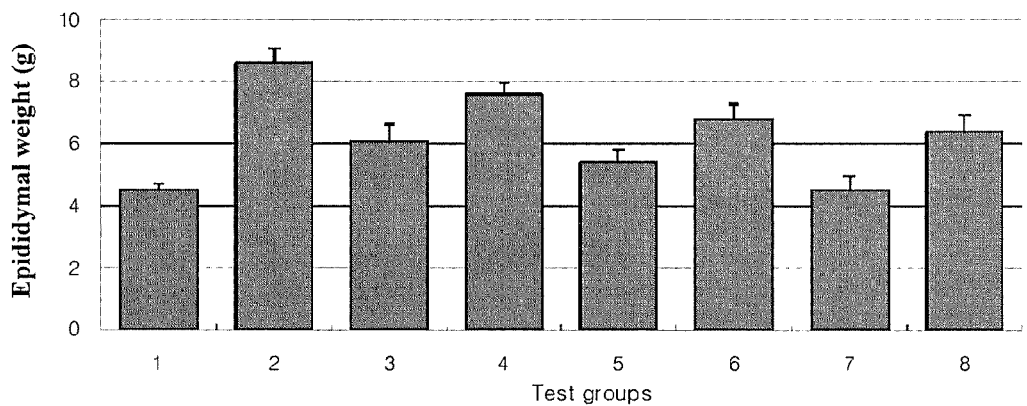
FIG. 10 is a graphic diagram showing the weight of epididymal fat extracted after the 8-week intake of the ginseng berry extract or the red ginseng extract together with a high-fat diet.

From the results of FIG. 10, it can be seen that, during the experiment period, the diet groups fed with the ginseng berry extract showed a decrease in epididymal adipose tissue weight compared to the high-fat diet. In addition, the epididymal adipose tissue weight of the ginseng berry extract diet groups was reduced in a manner dependent on the concentration of the ginseng berry extract, and the ginseng berry extract had an excellent effect on the inhibition of an increase in body fat compared to the red ginseng extract.

Experimental Example 10

Measurement of Expression of CPT-1

Figure 11:
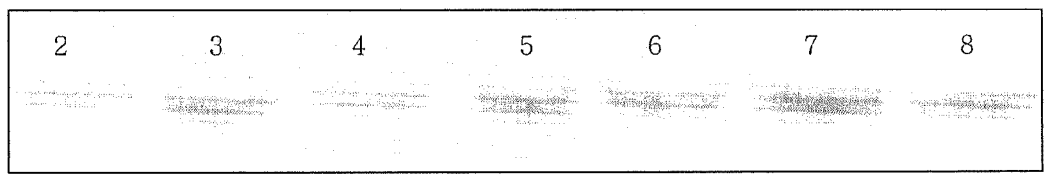
FIG. 11 shows the results of RT-PCR conducted to examine the expression of CPT-1 in the liver after the 8-week intake of the ginseng berry extract or the red ginseng extract together with a high-fat diet.

After the test groups 1-8 in Experimental Example 8 were fed with the diets, the animals were sacrificed and the liver of the animals was isolated. The isolated liver tissue was homogenized, and then the total RNA of the liver tissue was extracted using TRIZOL (Life Technologies$^\lambda$), Grand Island, NYU, USA) consisting of a mixture of phenol with guanidine isothiocyanate. From the extracted total RNA, the expression of CPT-1 mRNA was measured by RT-PCR, and the measurement results were quantified with densitometry and are shown in FIGS. 11 and 12.

Figure 12:
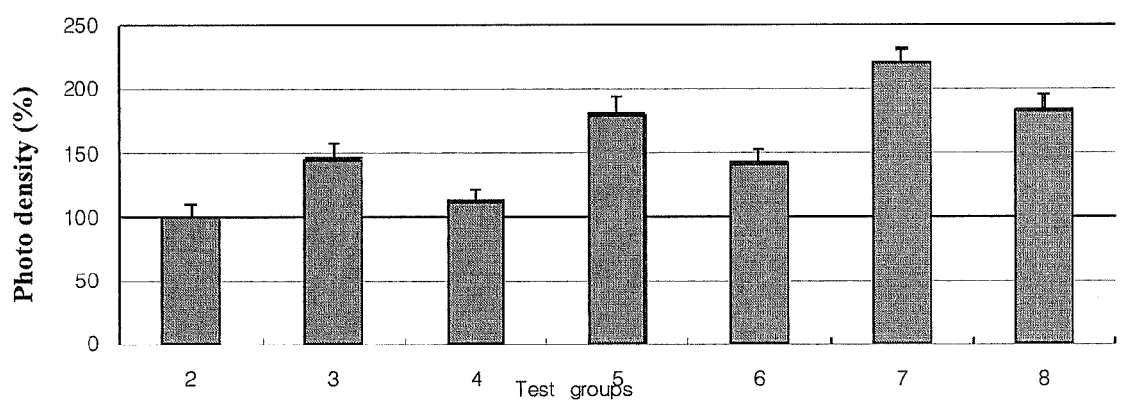
FIG. 12 is a graphic diagram showing the results of densitometric quantification of the results of FIG. 11.

As shown in FIG. 12, the expression of CPT-1 was higher in the ginseng berry extract diet groups than in the high-fat diet group, and thus the photo density of the ginseng berry extract diet groups was higher than that of the high-fat diet group. In addition, the expression of CPT-1 was significantly increased in a manner dependent on the concentration of the ginseng berry extract.

Hereinafter, formulation examples of the inventive composition will be described, but these formulation examples are illustrative only, and the scope of the present invention is not limited thereto.

Formulation Example 1

Skin Lotion

TABLE 29

| Components | Contents (wt %) |
|---|---|
| Purified water | Balance |
| *Ginseng* berry extract of Example 1 | 0.1 |
| Butyleneglycol | 2.0 |
| Propyleneglycol | 2.0 |
| Carboxyvinyl polymer | 0.1 |
| PEG-12 nonylphenylether | 0.2 |
| Polysorbate 80 | 0.4 |
| Ethanol | 10.0 |
| Triethanolamine | 0.1 |
| Preservative, pigment and fragrance | q.s. |

Formulation Example 2

Milk Lotion

TABLE 30

| Components | Contents (wt %) |
|---|---|
| Purified water | Balance |
| *Ginseng* berry extract of Example 1 | 0.1 |
| Beeswax | 4.0 |
| Polysorbate 60 | 1.5 |
| Sorbitan sesquioleate | 1.5 |
| Liquid paraffin | 0.5 |
| Montana 202 (manufactured by Seppic) | 5.0 |
| Glycerin | 3.0 |
| Butyleneglycol | 3.0 |
| Propyleneglycol | 3.0 |
| Carboxyvinyl polymer | 0.1 |
| Triethanolamine | 0.2 |
| Preservative, pigment and fragrance | q.s. |

Formulation Example 3

Massage Cream

TABLE 31

| Components | Contents (wt %) |
|---|---|
| Purified water | Balance |
| *Ginseng* berry extract of Example 1 | 0.1 |
| Beeswax | 10.0 |

TABLE 31-continued

| Components | Contents (wt %) |
|---|---|
| Polysorbate 60 | 1.5 |
| PEG 60 hydrogenated castor oil | 2.0 |
| Sorbitan sesquioleate | 0.8 |
| Liquid paraffin | 40.0 |
| Squalane | 5.0 |
| Montana 202 (manufactured by Seppic) | 4.0 |
| Glycerin | 5.0 |
| Butyleneglycol | 3.0 |
| Propyleneglycol | 3.0 |
| Triethanolamine | 0.2 |
| Preservative, pigment and fragrance | q.s. |

Formulation Example 4

Pack

TABLE 32

| Components | Contents (wt %) |
|---|---|
| Purified water | Balance |
| *Ginseng* berry extract of Example 1 | 0.1 |
| Polyvinyl alcohol | 13.0 |
| Sodium carboxymethylcellulose | 0.2 |
| Glycerin | 5.0 |
| Allantoin | 0.1 |
| Ethanol | 6.0 |
| PEG-12 nonylphenylether | 0.3 |
| Polysorbate 60 | 0.3 |
| Preservative, pigment and fragrance | q.s. |

Formulation Example 5

Injectable Formulation 50 mg of the ginseng berry extract of Example 1, a suitable amount of sterilized distilled water for injection and a suitable amount of a pH adjusting agent were mixed with each other. The mixture was placed into ampoules in an amount of 2 ml/ampoule according to a conventional method for preparing injectable formulations.

Formulation Example 6

Liquid Formulation 100 mg of the ginseng berry extract of Example 1, 10 g of high-fructose corn syrup, 5 g of mannitol and a suitable amount of purified water were mixed with each other. Lemon flavor was added to the mixture, and then purified water was the mixture to make a total volume of 100 mm. Then, the mixture was filled into a brown vial, thus preparing a liquid formulation.

Formulation Example 7

Soft Capsules 50 mg of the ginseng berry extract of Example 1, 80-140 mg of L-carnitine, 180 mg of soybean oil, 2 mg of palm oil, 8 mg of vegetable hydrogenated oil, 4 mg of yellow wax and 6 mg of lecithin were mixed with each other. The mixture was filled into capsules in an amount of 400 mg/capsule, thus preparing soft capsules.

Formulation Example 8

Tablets 50 mg of the ginseng berry extract of Example 1, 200 mg of galactooligosaccharide, 60 mg of lactose and 140 mg of maltose were mixed with each other. The mixture was granulated using a fluidized bed dryer, and 6 mg of sugar ester was added thereto. The granules were tableted using a tableting machine, thus preparing tablets.

Formulation Example 9

Granules 50 mg of the ginseng berry extract of Example 1, 250 mg of anhydrous crystalline glucose and 550 mg of starch were mixed with each other. The mixture was formed into granules using a fluidized bed granulator, and then packaged.

Formulation Example 10

Drinks 50 mg of the ginseng berry extract of Example 1, 10 g of glucose, 0.6 g of citric acid and 25 g of liquid oligosaccharide were mixed with each other, and then 300 ml of purified water was added thereto. The mixture was filled into bottles in an amount of 200 ml/bottle. Then, the bottles were sterilized at 130° C. for 4-5 seconds, thus preparing drinks.

The invention claimed is:

1. A method of combating inflammation of the skin, comprising
   (a) topically applying to the skin of a subject in need of same an effective amount of a ginseng berry extract prepared by a method consisting of the following steps:
   1) drying flesh and skin of ginseng berries after removing the seeds therefrom; and
   2) adding water or ethanol to the dried material of step 1), extracting the solution under reflux, filtering the extract, and concentrating the filtrate under reduced pressure, and
   (b) reducing the production of inflammatory factors.

2. A method of combating inflammation of the skin, comprising
   (a) topically applying to the skin of a subject in need of same an effective amount of a ginseng berry extract prepared by a method consisting of the following steps:
   1) drying flesh and skin of ginseng berries after removing the seeds therefrom; and
   2) adding water or ethanol to the dried material of step 1), extracting the solution under reflux, filtering the extract, and concentrating the filtrate under reduced pressure, and
   (b) reducing the biosynthesis of COX-2, Tumor Necrosis Factor-alpha, or both.

3. A method of combating inflammation of the skin, comprising
   (a) topically applying to the skin of a subject in need of same an effective amount of a ginseng berry extract prepared by the method consisting of the following steps:
   1) drying flesh and skin of ginseng berries after removing the seeds therefrom; and 2) adding water or ethanol to the dried material of step 1), extracting the solution under reflux, filtering the extract, and concentrating the filtrate under reduced pressure, and
(b) reducing nitrogen oxide biosynthesis.

* * * * *